(12) United States Patent
Kiesel et al.

(10) Patent No.: US 8,153,950 B2
(45) Date of Patent: Apr. 10, 2012

(54) OBTAINING SENSING RESULTS AND/OR DATA IN RESPONSE TO OBJECT DETECTION

(75) Inventors: Peter Kiesel, Palo Alto, CA (US); Markus Beck, Palo Alto, CA (US); Joerg Martini, San Francisco, CA (US); Michael Bassler, Erlangen (DE); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 542 days.

(21) Appl. No.: 12/337,771

(22) Filed: Dec. 18, 2008

(65) Prior Publication Data

US 2010/0155572 A1 Jun. 24, 2010

(51) Int. Cl.
*G01J 1/42* (2006.01)
*F21V 9/16* (2006.01)
*G01N 21/25* (2006.01)

(52) U.S. Cl. .................. 250/208.2; 250/459.1; 356/417

(58) Field of Classification Search .............. 250/223 B, 250/223 R, 231.13–231.18, 208.1, 214 R, 250/208.2, 458.1, 459.1, 573; 341/8, 9, 13, 341/14; 356/73, 416, 417, 419; 359/238, 359/830
See application file for complete search history.

(56) References Cited

U.S. PATENT DOCUMENTS

| | | | |
|---|---|---|---|
| 4,573,796 A | 3/1986 | Martin et al. | |
| 5,151,585 A | 9/1992 | Siebert | |
| 5,243,614 A | 9/1993 | Wakata et al. | |
| 5,254,919 A | * 10/1993 | Bridges et al. | 318/560 |
| 5,324,401 A | 6/1994 | Yeung et al. | |
| 5,370,842 A | 12/1994 | Miyazaki et al. | |
| 5,445,934 A | 8/1995 | Fodor et al. | |
| 5,491,347 A | 2/1996 | Allen et al. | |
| 5,674,698 A | 10/1997 | Zarling et al. | |
| 5,682,038 A | 10/1997 | Hoffman | |
| 5,760,900 A | 6/1998 | Ito et al. | |

(Continued)

FOREIGN PATENT DOCUMENTS

WO WO 99/54730 A1 10/1999
(Continued)

OTHER PUBLICATIONS

Office communication in U.S. Appl. No. 12/024,490, mailed Nov. 2, 2009, 14 pages.

(Continued)

*Primary Examiner* — Georgia Y Epps
*Assistant Examiner* — Don Williams
(74) *Attorney, Agent, or Firm* — Stanzione & Kim, LLP

(57) ABSTRACT

An encoder/sensor can obtain sensing results from objects in an encoding/sensing region; a trigger detector can respond to objects in a trigger detection region, providing respective trigger signals; and a relative motion component can cause relative motion of objects into the trigger detection region, from it into the encoding/sensing region, and within the encoding/sensing region. In response to an object's trigger signal, control circuitry can cause the encoder/sensor and/or the relative motion component to operate so that the encoder/sensor obtains sensing results indicating a time-varying waveform and processing circuitry can obtain data from the sensing results indicating a time-varying waveform. The time-varying waveform can include information resulting from the relative motion within the encoding/sensing region. The encoder/sensor and trigger detector can be implemented, for example, with discrete components or as sets of cells in a photosensing array on an integrated circuit.

25 Claims, 16 Drawing Sheets

U.S. PATENT DOCUMENTS

| | | | |
|---|---|---|---|
| 5,793,485 | A | 8/1998 | Gourley |
| 5,880,474 | A | 3/1999 | Norton et al. |
| 5,945,676 | A | 8/1999 | Khalil et al. |
| 6,091,502 | A | 7/2000 | Weigl et al. |
| 6,558,945 | B1 | 5/2003 | Kao |
| 6,580,507 | B2 | 6/2003 | Fry et al. |
| 6,628,390 | B1 | 9/2003 | Johnson |
| 6,906,792 | B2 | 6/2005 | Ortyn et al. |
| 7,195,797 | B2 | 3/2007 | Mearini et al. |
| 7,252,360 | B2 | 8/2007 | Hersch et al. |
| 7,291,824 | B2 | 11/2007 | Kiesel et al. |
| 7,298,478 | B2 | 11/2007 | Gilbert et al. |
| 7,355,699 | B2 | 4/2008 | Gilbert et al. |
| 7,358,476 | B2 | 4/2008 | Kiesel et al. |
| 7,386,199 | B2 | 6/2008 | Schmidt et al. |
| 7,420,677 | B2 | 9/2008 | Schmidt et al. |
| 7,433,552 | B2 | 10/2008 | Kiesel et al. |
| 7,440,101 | B2 | 10/2008 | Auer et al. |
| 7,466,409 | B2 | 12/2008 | Scherer et al. |
| 7,471,399 | B2 | 12/2008 | Kiesel et al. |
| 7,479,625 | B2 | 1/2009 | Kiesel et al. |
| 7,502,123 | B2 | 3/2009 | Schmidt et al. |
| 7,522,786 | B2 | 4/2009 | Kiesel et al. |
| 7,547,904 | B2 | 6/2009 | Schmidt et al. |
| 7,554,673 | B2 | 6/2009 | Kiesel et al. |
| 7,701,580 | B2 | 4/2010 | Bassler et al. |
| 2002/0155485 | A1 | 10/2002 | Kao |
| 2003/0169311 | A1* | 9/2003 | Kong Leong et al. ........... 347/19 |
| 2004/0027462 | A1 | 2/2004 | Hing |
| 2004/0038386 | A1 | 2/2004 | Zesch et al. |
| 2004/0067167 | A1 | 4/2004 | Zhang et al. |
| 2007/0076210 | A1 | 4/2007 | Kiesel et al. |
| 2007/0146704 | A1 | 6/2007 | Schmidt et al. |
| 2007/0166725 | A1* | 7/2007 | McBride et al. .................. 435/6 |
| 2008/0181827 | A1 | 7/2008 | Bassler et al. |
| 2008/0183418 | A1 | 7/2008 | Bassler et al. |
| 2008/0186488 | A1 | 8/2008 | Kiesel et al. |
| 2008/0186492 | A1 | 8/2008 | Kiesel et al. |
| 2008/0186500 | A1 | 8/2008 | Schmidt et al. |
| 2008/0186503 | A1 | 8/2008 | Kiesel et al. |
| 2008/0186504 | A1 | 8/2008 | Kiesel et al. |
| 2008/0186508 | A1 | 8/2008 | Kiesel et al. |
| 2008/0187011 | A1 | 8/2008 | Kiesel et al. |
| 2008/0197272 | A1 | 8/2008 | Kiesel et al. |
| 2008/0299327 | A1 | 12/2008 | Salleo et al. |
| 2009/0190121 | A1 | 7/2009 | Hegyi et al. |
| 2009/0194705 | A1 | 8/2009 | Kiesel et al. |
| 2009/0195773 | A1 | 8/2009 | Bassler et al. |
| 2009/0220189 | A1 | 9/2009 | Kiesel et al. |

FOREIGN PATENT DOCUMENTS

| | | |
|---|---|---|
| WO | WO 00/62050 A1 | 10/2000 |
| WO | WO 02/25269 A2 | 3/2002 |
| WO | WO 2005/108963 A1 | 11/2005 |

OTHER PUBLICATIONS

Office communication in U.S. Appl. No. 11/698,409, mailed Nov. 17, 2009, 18 pages.

Office communication in U.S. Appl. No. 12/025,394, mailed Jan. 22, 2010, 7 pages.

Office communication in U.S. Appl. No. 12/023,436, mailed Feb. 5, 2010, 16 pages.

Amendment in U.S. Appl. No. 12/023,436, submitted Mar. 23, 2010, 24 pages.

Office communication in U.S. Appl. No. 12/023,436, mailed Apr. 16, 2010, 8 pages.

Amendment in U.S. Appl. No. 12/025,394, submitted Apr. 22, 2010, 17 pages.

Office communication in U.S. Appl. No. 11/698,409, mailed Jun. 11, 2010, 21 pages.

Cheung, K., Gawad, S., and Renaud, P., "Impedance Spectroscopy Flow Cytometry: On-Chiip Label-Free Cell Differentiation", Cytometry Part A, vol. 65A, 2005, pp. 124-132.

"Flow Cytometry", printed from www.wellscenter.iupui.edu/MMIA on Jan. 29, 2008, 4 pages.

Stanford Research Systems, "Optical Chopper—SRO540—Optical Chopper System", printed from thinkSRS.com Website on Oct. 21, 2008, 2 pages.

"Lab-on-a-Chip, Advances in Microarray TEchnology and Advances in Biodefense Technology", brochure, May 7-8, 2008, 6 pages.

Office communication in U.S. Appl. No. 12/022,485, mailed Jul. 31, 2009, 5 pages.

Response to Restriction Requirement in U.S. Appl. No. 12/022,485, submitted Aug. 27, 2009, 20 pages.

Office communication in U.S. Appl. No. 12/023,436, mailed Jun. 12, 2009, 20 pages.

Amendment in U.S. Appl. No. 12/023,436, submitted Sep. 3, 2009, 29 pages.

Office communication in U.S. Appl. No. 12/024,490, mailed Jul. 22, 2009, 16 pages.

Amendment After Final Rejection in U.S. Appl. No. 12/024,490, submitted Sep. 22, 2009, 28 pages.

Office communication in U.S. Appl. No. 11/702,321, mailed Feb. 20, 2009, 19 pages.

Amendment in U.S. Appl. No. 11/702,321, submitted May 8, 2009, 21 pages.

Notice of Allowance and Fee(s) Due in U.S. Appl. No. 11/702,321 mailed Aug. 11, 2009, 20 pages.

Office communication in U.S. Appl. No. 11/702,320, mailed Aug. 12, 2009, 9 pages.

Shapiro, H. M., Practical Flow Cytometry, Fourth Edition, Wiley-Liss, 2003, Table of Contents and pp. 49-59, 124-183, 191-197, 345, and 364-366.

Hoffman, R. A., "Flow Cytometry: Instrumentation, Applications, Future Trends and Limitations", Springer Series on Fluorescence, vol. 6, 2008, pp. 307-342.

Office communication in U.S. Appl. No. 12/023,436, mailed Dec. 23, 2008, 15 pages.

Amendment in U.S. Appl. No. 12/023,436, submitted Mar. 23, 2009, 22 pages.

Office communication in U.S. Appl. No. 12/022,485, mailed Jan. 16, 2009, 18 pages.

Amendment in U.S. Appl. No. 12/022,485, submitted Apr. 15, 2009, 30 pages.

Office communication in U.S. Appl. No. 12/024,490, mailed Dec. 24, 2008, 12 pages.

Amendment in U.S. Appl. No. 12/024,490, submitted Mar. 24, 2009, 32 pages.

Amendment in U.S. Appl. No. 11/698,409, submitted May 17, 2010, 16 pages.

* cited by examiner

OBTAINING SENSING RESULTS AND/OR DATA IN RESPONSE TO OBJECT DETECTION

The following applications, each of which is hereby incorporated by reference in its entirety, might be regarded as related to this application: "Sensing Photon Energies Emanating from Channels or Moving Objects", U.S. patent application Ser. No. 11/315,386, now published as U.S. Patent Application Publication No. 2007/0146704; "Method and System for Evaluation of Signals Received from Spatially Modulated Excitation and Emission to Accurately Determine Particle Positions and Distances", U.S. patent application Ser. No. 11/698,338, now published as U.S. Patent Application Publication No. 2008/0183418; "Method and System Implementing Spatially Modulated Excitation or Emission for Particle Characterization with Enhanced Sensitivity", U.S. patent application Ser. No. 11/698,409, now published as U.S. Patent Application Publication No. 2008/0181827; "Obtaining Information From Optical Cavity Output Light", U.S. patent application Ser. No. 11/702,249, now published as U.S. Patent Application Publication No. 2008/0186500; "Photosensing Optical Cavity Output Light", U.S. patent application Ser. No. 11/702,250, now published as U.S. Patent Application Publication No. 2008/0186503; "Distinguishing Objects", U.S. patent application Ser. No. 11/702,328, now published as U.S. Patent Application Publication No. 2008/0186488; "Encoding Optical Cavity Output Light", U.S. patent application Ser. No. 11/702,363, now published as U.S. Patent Application Publication No. 2008/0186492; "Moving Analytes and Photosensors", U.S. patent application Ser. No. 11/702,470, now published as U.S. Patent Application Publication No. 2008/0186504; "Surface Energy Control Methods for Color Filter Printing", U.S. patent application Ser. No. 11/755,717; "Producing Sandwich Waveguides", U.S. patent application Ser. No. 11/777,661; "Producing Fluidic Waveguides", U.S. patent application Ser. No. 11/777,712; "Obtaining Information from Time Variation of Sensing Results", U.S. patent application Ser. No. 12/022,485; "Providing Time Variation in Emanating Light", U.S. patent application Ser. No. 12/023,436; "Transmitting/Reflecting Emanating Light with Time Variation", U.S. patent application Ser. No. 12/024,490; "Producing Filters with Combined Transmission and/or Reflection Functions", U.S. patent application Ser. No. 12/025,394; "Sensing Photons From Objects in Channels", U.S. patent application Ser. No. 12/098,584, now published as U.S. Patent Application Publication No. 2008/0197272; "Obtaining Sensing Results Indicating Time Variation", U.S. patent application Ser. No. 12/337,737; and "Causing Relative Motion", U.S. patent application Ser. No. 12/337,796.

BACKGROUND OF THE INVENTION

The present invention relates generally to techniques that, in response to object detection, obtain information. More specifically, techniques can respond to object detection by obtaining encoded sensing results or data that indicate time-varying waveforms with information.

Various techniques have been proposed for obtaining information in response to object detection. For example, U.S. Pat. No. 7,358,476 describes a fluidic structure with a channel along which is a series of sensing components to obtain information about objects traveling within the channel, such as droplets or other objects carried by fluid. A sensing component includes a set of cells that photosense respective subranges of a range of photon energies that emanate from objects. Positioned upstream is a series of triggering photodetectors or another type of object detector, and a photosensor array could also include uncoated trigger cells upstream from a line of the subrange cells. A processor can perform pre-sensing readout to obtain information for a sensing readout such as each object's position and speed or an appropriate sensing period for each object; the processor can use this information during a sensing readout operation in which it receives information about objects from the sensing components and uses it to obtain spectral information. Similar techniques are described, for example, in U.S. Pat. Nos. 7,291,824, 7,386,199, and 7,420,677 and in U.S. Patent Application Publication Nos. 2007/0146704 and 2008/0197272.

It would be advantageous to have improved techniques for obtaining information in response to object detection.

SUMMARY OF THE INVENTION

The invention provides various exemplary embodiments, including systems, methods, and apparatus. In general, the embodiments involve responding to objects and obtaining or providing encoded sensing results and/or data.

These and other features and advantages of exemplary embodiments of the invention are described below with reference to the accompanying drawings.

DETAILED DESCRIPTION

Figure 1:
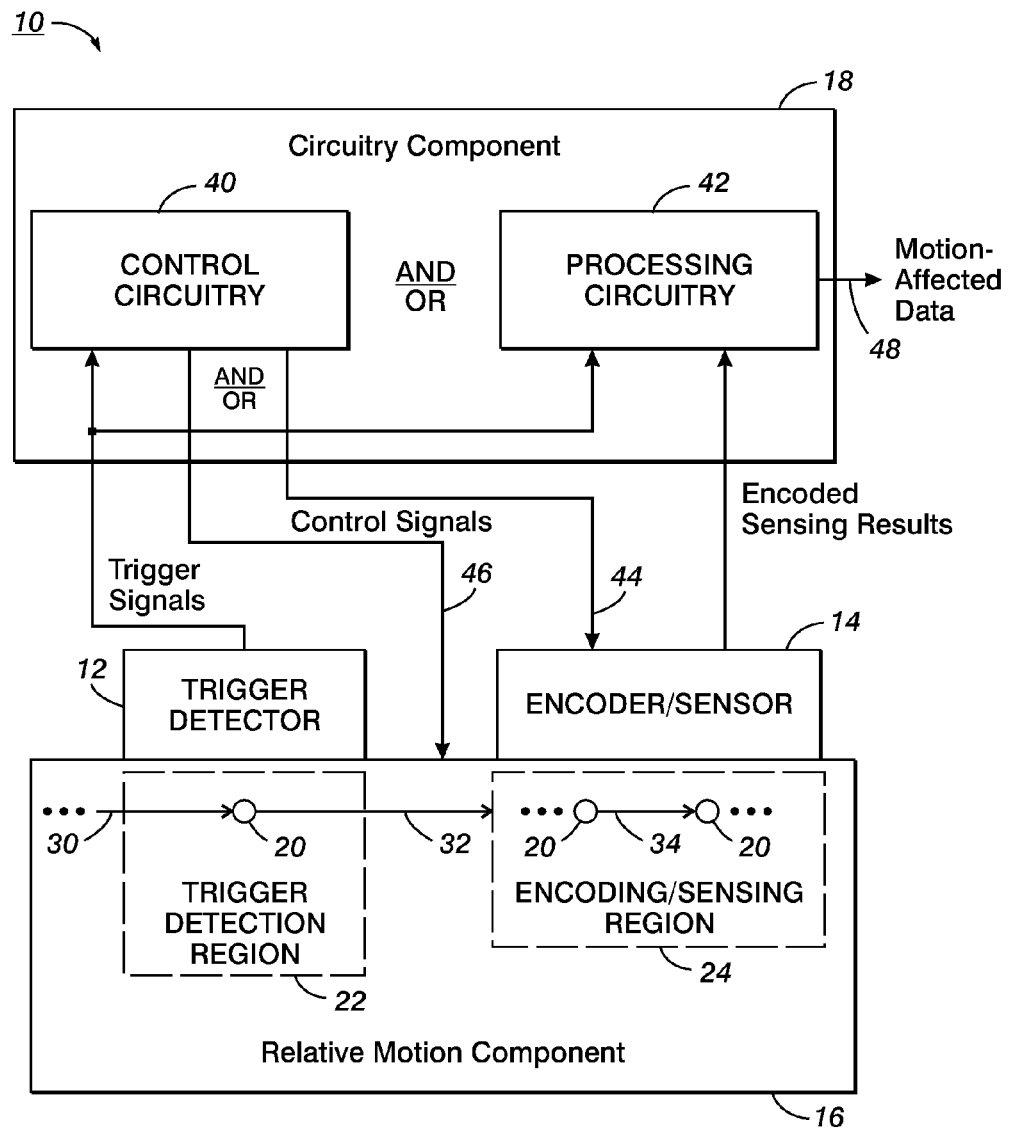
FIG. 1 is a schematic diagram illustrating general features of a system in which a trigger detector provides trigger signals and in which encoded sensing results and/or data indicate at least one time-varying waveform with information resulting from an object's relative motion within an encoding/sensing region.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

The term "sensing" is used herein in the most generic sense of obtaining information from a physical stimulus; sensing therefore includes actions such as detecting, measuring, and so forth. A "sensor" is a device that performs sensing. Data or other signals that indicate or include results of sensing are sometimes referred to herein as "sensing results". An operation "obtains" sensing results if the operation makes the sensing results available in any appropriate way in the context; for example, an operation could obtain sensing results by producing sensing results, by providing or transferring sensing results from one position or time to another, by accessing sensing results that are stored in computer memory or on a storage medium or captured in any other machine-accessible form, or in any other way appropriate to the context.

In general, the various types of sensors described herein provide sensing results in the form of electrical signals unless otherwise indicated or required by the context. The term "electrical signal" is used herein to encompass any signal that transfers information from one position or region to another in an electrical, electronic, electromagnetic, or magnetic form. Electrical signals may be conducted from one position or region to another by electrical or magnetic conductors, but the broad scope of electrical signals also includes light and other electromagnetic forms of signals and other signals transferred through non-conductive regions due to electrical, electronic, electromagnetic, or magnetic effects. In general, the broad category of electrical signals includes both "analog" and "digital" signals: An "analog" electrical signal includes information in the form of a continuously variable physical quantity, such as voltage; a "digital" electrical signal, in contrast, includes information in the form of discrete values of a physical characteristic, which could also be, for example, voltage.

An "encoder/sensor", which may sometimes be referred to as an "encoding/sensing component" or an "encoding/sensing arrangement", falls within the above definition of a sensor, but provides "encoded sensing results", meaning that the encoder/sensor also performs operations that encode information in the sensing results such that data or other signals indicating the sensing results also indicate the encoded information; meanings of "encode" and related terms are discussed in greater detail below in relation to exemplary implementations. In exemplary implementations described herein, the encoded information can, for example, be information resulting from relative motion between objects and components or regions. operates to encode and sense information, The various exemplary implementations described below address problems that arise in operating encoder/sensors. For example, a number of techniques have been proposed in which encoding occurs in an encoder/sensor due to relative motion of objects within a "patterned environment" and in which sensing is performed during the relative motion to obtain time-varying sensing results. As used here, the term "patterned environment" means an environment with a pattern that is relatively stable while several or many objects have relative motion within the environment; a patterned environment could result from a relatively stable pattern in one or more of various features of the environment—excitation of objects in the environment, displacement of objects within the environment, masking or filtering of light emanating from objects in the environment, impedance-based sensing of objects in the environment, photosensing of light emanating from objects in the environment, and so forth.

Although encoding due to relative motion within a patterned environment can be performed in many ways, it is constrained by the requirement of a stable pattern: For example, the pattern cannot be adjusted for each object's position relative to the environment, for each object's timing in entering the environment, for each object's speed or other displacement relative to the environment, for each object's size or mass, and so forth. Furthermore, the proposed patterned environment techniques generally encode information with only one patterning of the environment at a time, an approach that limits the amount of information that can be encoded within a given amount of time, i.e. encoding bandwidth. In these and other ways, patterned environment techniques and other previous encoding/sensing techniques are not sufficiently flexible and robust to provide all the types of encoding and sensing that would be useful.

In addressing these limitations, exemplary implementations described below employ trigger detectors that provide trigger signals in response to each distinguishable object. The exemplary implementations respond to trigger signals in various ways. In doing so, the exemplary implementations can overcome limitations of patterned environments and can also provide new encoding/sensing techniques not previously available or proposed.

In some exemplary implementations, control circuitry responds to trigger signals. For example, control circuitry can respond to an object's trigger signal by providing control signals that cause the encoder/sensor and/or a relative motion component to operate so that the encoder/sensor provides encoded sensing results. The encoded sensing results can indicate at least one time-varying waveform with information resulting from the object's relative motion within an encoding/sensing region relative to the encoder/sensor.

Similarly, in some exemplary implementations, an encoder/sensor responds to an object's trigger signal, directly or in response to control signals, by providing time variation or by combining sensing results. For example, an encoder/sensor could include one or more of excitation circuitry providing time-varying excitation, displacement circuitry providing time-varying displacement, and filter circuitry providing time-varying filtering of emanating light; these types of time variation could be provided in response to the object's trigger signal, resulting in encoded information. Or an encoder/sensor could include sensor circuitry that, in response to the object's trigger signal, reads out and combines photosensed quantities from a subsequence of a longitudinal sequence of photosensing elements, providing combined sensing results that indicate a time-varying waveform as described above.

Also, in some exemplary implementations, a relative motion component includes one or more of a motion device, a fluidic device, a scanner device, and a rotary device that, in response to control signals, can provide time-varying displacement. A scanner device, for example, can provide relative motion in a scanning direction between a support structure supporting one or more objects and an encoder/sensor; in response to an object's trigger signal, the scanner device can provide time-varying displacement in one or more of three directions, including the scanning direction, a first lateral direction in which distance between encoder/sensor and the object is not changed, and a second lateral direction in which distance between encoder/sensor and the object changes. Similar, a rotary device can provide relative motion in a direction of rotation between a support structure supporting one or more objects and an encoder/sensor; in response to an object's trigger signal, the rotary device can provide time-varying displacement in one or more of three directions, including the rotation direction, a radial direction in which distance between encoder/sensor and axis of rotation changes, and a lateral direction in which distance between encoder/sensor and the object changes.

In some exemplary implementations, processing circuitry responds to trigger signals. For example, the processing circuitry can respond to an object's trigger signal by obtaining data from sensing results, where the data indicate at least one time-varying waveform as described above. Although this technique can be used with a stable patterned environment without time variation and without combining sensing results as described above, it can also be used in combination with time variation and/or combining sensing results.

By providing these capabilities, the exemplary implementations alleviate the limitations of patterned environment techniques and other previous encoding/sensing techniques. For example, some of the exemplary implementations allow adjustment of a patterned environment for each object, such as in response to the object's position, relative speed, timing, size, mass, and so forth. Also, some exemplary implementations allow increased encoding bandwidth by storing sensing results and then processing the stored sensing results with two or more different patterns. Further, some exemplary implementations provide new types of encoding/sensing not previously known.

As noted above, the exemplary implementations generally employ trigger detectors. In contrast to an encoder/sensor, a "trigger detector", which may sometimes be referred to as a "trigger detecting component" or a "trigger detecting device", is a sensor that responds to a detected condition or event by providing a signal indicating the condition or event's detection, typically referred to herein as a "trigger signal". For example, a trigger detector could provide a trigger signal when it detects a distinguishable object in a particular region. A trigger detector can be a discrete component or device, or it could be provided by operations that read out a trigger part of a photosensing array or in another appropriate way.

In contrast to an encoder/sensor, a "trigger detector", which may sometimes be referred to as a "trigger detecting component" or a "trigger detecting device", is a sensor that responds to a detected condition or event by providing a signal indicating the condition or event's detection, typically referred to herein as a "trigger signal". For example, a trigger detector could provide a trigger signal when it detects a distinguishable object in a particular region. A trigger detector can be a discrete component or device, or it could be provided by operations that read out a trigger part of a photosensing array or in another appropriate way. More generally, the term "trigger detector" is used herein to refer to any of a wide variety of devices and components that perform operations as described, whether or not otherwise referred to with the same terminology, and the term "trigger signal" similarly is not limited to signals that are referred to with the same terminology.

"Light" refers herein to electromagnetic radiation of any wavelength or frequency; unless otherwise indicated, a specific value for light wavelength or frequency is that of light propagating through vacuum. Light that can include information is sometimes referred to herein as an "optical signal".

"Photosensing" is sensing of light. A "photosensor" is accordingly an electronic device that performs photosensing. More specifically, if optical signals include information, a photosensor that receives the optical signals may be able to sense the information and provide sensing results that indicate or include the information; sensing results from a photosensor often indicate "photosensed quantities", meaning quantities that indicate a characteristic of photosensed light, such as an intensity, a spectral characteristic, etc. A surface at which photosensing occurs is referred to herein as a "photosensitive surface".

Another type of sensing relevant to some exemplary implementations described below is "impedance-based sensing", meaning sensing that obtains information from variation in resistance (or inversely, conductivity), capacitance, inductance, or another form of electrical impedance that varies in response to a physical stimulus such as an electrical or magnetic characteristic of an object or of an object's environment. As used herein, "impedance-based sensing" includes sensing with Hall effect sensors and similar types of sensors.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry, and a given hardware component can similarly be replaced by equivalent processor operations controlled by software.

Circuitry can be described based on its operation or other characteristics. For example, circuitry that performs control operations is sometimes referred to herein as "control circuitry" and circuitry that performs processing operations is sometimes referred to herein as "processing circuitry". Also, "readout circuitry" refers herein to circuitry that operates to read out photosensed quantities, while "readout/combine circuitry" refers herein to circuitry operates as readout circuitry and also operates to combine readout quantities. As used herein, an operation "combines" quantities in any way that includes the quantities in a single item of data, a single data structure, or a single combination of items of data or data structures that can be accessed together, such as in sequence; for example, two quantities can be combined by arithmetic operations such as addition, subtraction, multiplication, division, averaging, and so forth, or by concatenating them, linking them, or otherwise ordering them into a sequence or data structure.

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations of ICs and photosensing components described herein include features characterized as "cells" (or "elements") and "arrays", terms that are used with related meanings: An "array" is an arrangement of "cells" or "elements"; unless otherwise indicated by the context, such as for a biological cell, the words "cell" and "element" are used interchangeably herein to mean a cell or an element of an array. An IC includes a "photosensor array" if the IC includes an array of cells, and at least some of the cells include respective photosensors.

Some of the implementations below are described in terms of "rows" and "columns", but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

FIG. 1 shows general features of techniques in which sensing results and/or data indicating time-varying waveforms can be obtained. The techniques are illustratively implemented in system 10, but could be similarly implemented in various apparatus and methods. System 10 illustratively includes trigger detector 12, encoder/sensor 14, relative motion component 16, and circuitry component 18.

As used herein, the term "system" refers to a combination of two or more parts or components that can perform an operation together. A system may be characterized by its operation. A system may include one or more parts or components that can operate automatically, but, as used herein, the term "system" can include a system with components that operate non-automatically, automatically, partially automatically, or any combination.

Within a system, apparatus, device, or other article, components and parts may be referred to in a similar manner. In addition to encoder/sensors and trigger detectors as defined above, other components of a system, for example, can include a "relative motion component" that operates to cause some sort of relative motion. Various other components that can occur within encoder/sensors are also identified by their operations, including "excitation components", "displacement components", "filter components", and "sensing components" as described below. In addition, a component or part may be identified by characteristics other than its operation; for example, a "circuitry component" is a component that includes circuitry.

The term "excitation component" refers herein to a part or component that provides excitation of any appropriate type, in response to which objects emanate light. For example, illumination of various kinds can cause objects to emanate light, i.e. to photoluminesce, so that many excitation components are light sources; another example of excitation is an electron beam that causes objects to emanate light, i.e. to cathodoluminesce. Other types of excitation can also be provided, within the scope of the techniques described herein, and further examples of excitation are described in co-pending U.S. patent application Ser. No. 12/023,436, entitled "Producing Time Variation in Emanating Light" and incorporated herein by reference; as described in that application, categories of longitudinal sequences of excitation region include, for example, periodic patterns, chirp patterns, random patterns, and so forth, and various other categories could be identified: As used herein regarding excitation patterns, the term "random" refers to a pattern that is non-periodic over the entire length of a longitudinal sequence of excitation regions; in contrast, a "periodic" sequence has at least one pattern that repeats more than once across the sequence's longitudinal length; and "chirp" sequences meet the above definition of random but can, with linearly varying time-scaling, meet the above definition of periodic, in effect being a sequence of periods of linearly changing frequency or wavelength.

The term "displacement component" refers herein to a part or component that provides displacement of any appropriate type, typically displacement of objects having relative motion within an encoding/sensing region; displacement that is part of relative motion is sometimes referred to herein as "relative displacement". Although a relative motion component could be thought of as a type of displacement component, a given system might include both a relative motion component and a displacement component or might include a single device that can operate both as a relative motion component and as a displacement component, and a relative motion component might include one or more displacement components that each provide a respective type of relative displacement; exemplary implementations described below illustrate these possibilities. For example, a fluidic device could operate as a relative motion component, providing an object's relative motion in a longitudinal direction within a channel, and a motion device could operate as a displacement component, causing the channel walls along an encoding/sensing region to move relative to the object such as in a lateral direction not parallel to the longitudinal direction. Or a scanner or rotary device could operate as a relative motion component providing an object's relative motion in a scanning direction or in a direction of rotation, and could also operate as a displacement component providing relative displacement during the object's relative motion within an encoding/sensing region.

The term "optical filter" or simply "filter component", "filter", or "mask" refers herein to a light-transmissive part or component that transmits light in accordance with a respective criterion, sometimes referred to herein as a filter's "type". For example, one general category of filters is "band pass filters", referring to types of filters that, across some application's range of photon energies, e.g. a range of wavelengths or frequencies such as the visible range, preferentially transmit light within a subrange, sometimes referred to as a "band"; a band pass filter's type can therefore be specified by specifying the band or subrange of photon energies in which it transmits. A "blocking filter", which does not transmit any light in an application's range, can be viewed as a band pass filter with a band of zero bandwidth, while a "transparent filter", which transmits all light in an application's range, can be viewed as a band pass filter with a band that includes the entire range. Other types of filters can also be provided, within the scope of the techniques described herein, and further examples of filters are described in co-pending U.S. patent application Ser. No. 12/024,490, entitled "Transmitting/Reflecting Emanating Light with Time Variation" and incorporated herein by reference; as described in that application, categories of filters include, for example, shadow masks, periodic masks, chirp masks, random masks, and so forth, and various other categories could be identified: As used herein regarding filter components, the term "random" refers to a pattern that is non-periodic over the entire length of a longitudinal sequence of filters; in contrast, a "periodic" filter has at least one pattern that repeats more than once across the filter's longitudinal length; and "chirp" patterns meet the above definition of random but can, with linearly varying time scaling, meet the above definition of periodic, in effect being a sequence of periods of linearly changing frequency or wavelength. A "shadow mask" is not a band pass filter, but rather an intensity-based filter that, within a photon energy range of interest, transmits light of all energies, but with different parts of the filter transmitting the light at different intensities, such as black and white and/or different gray scales.

The term "sensing component" refers herein to a sensor, as described above, or to a component that includes a sensor together with at least some related circuitry. As with excitation and filter components, sensing components can be categorized in relation to sensing patterns, some examples of which are described below. In general, categories of sensing patterns can similarly include, for example, periodic patterns, chirp patterns, random patterns, and so forth, and various other categories could be identified.

In the example illustrated in FIG. 1, trigger detector 12 responds to object 20 in trigger detection region 22, providing a respective trigger signal for object 20 to circuitry component 18. In other words, trigger detector 12 is a component or device that detects presence of objects in region 22. Similarly, encoder/sensor 14 responds to object 20 in encoding/sensing region 24, providing encoded sensing results for object 20 to circuitry component 18.

In this context, the term "region" refers to a connected set of points or positions in space. In the particular examples, each of regions 22 and 24 is a region that is "relative to" a component or device, meaning that the region has an approximately constant spatial relationship to the component or device and accordingly would move with the component or device if the component or device moved; for example, trigger detection region 22 is a region relative to trigger detector 12, as suggested in FIG. 1 by its position adjacent trigger detector 12, and encoding/sensing region 24 is similarly a region relative to encoder/sensor 14, as similarly suggested by its position adjacent encoder/sensor 14. Region 22 may be thought of as the region relative to trigger detector 12 within which objects can be detected to an appropriate level of accuracy for a given application, and region 24 may similarly be thought of as the region relative to encoder/sensor 14 within which an object can interact with encoder/sensor 14 such that information can be encoded and sensed through the interaction to an appropriate level of accuracy for a given application. In embodiments described herein, objects move into regions, from one region into another, and within regions; accordingly, regions as described herein are not in general bounded by structures that would interfere with such movements, but each trigger detection region and encoding/sensing region could have geometrically defined, imaginary boundaries within which a given level of accuracy can be obtained by the respective trigger detector or encoder/sensor.

Detection by trigger detector 12 and encoding and sensing by encoder/sensor 14 could be performed by interacting with object 20 in various ways. For example, light could emanate from object 20, such as by emission, scattering (including, e.g. reflection), or transmission, and a portion of the emanating light could be received by photosensors in detector 12 and encoder/sensor 14. In general, such emanating light includes light within an application's range of photon energies, meaning that techniques as in FIG. 1 can be successfully used in a given application, e.g. flow cytometry, bio-chip readout, scanning of a support structure bearing spots or other objects, or any suitable kind of analyte detection, even though emanating light might also include photon energies that are outside the application's range and that might not interact with photosensors in detector 12 and encoder/sensor 14 in the same way as light in the application's range. In other examples, object 20 could interact electrically or magnetically with impedance-based sensing elements in one or both of detector 12 and encoder/sensor 14. In general, a sensor of any kind obtains sensing results "from" objects in a sensing region when the sensing results include information resulting from any such interaction between the sensor and the objects while the objects are in the sensing region.

The term "object" is used herein in the general sense of any thing from which a trigger detector, an encoder/sensor, or another type of detector or sensor of objects can obtain information. In contexts with more than one object, the term "distinguishable object" is used herein to refer only to an object that is configured relative to other objects and/or has other characteristics such that the trigger detector, encoder/sensor, or other type of detector or sensor of objects being used can obtain information from the object substantially separately from information obtained from other objects. For example, if objects in a set are approximately the same in speed, mass, structure, etc. and therefore would not be distinguishable if more than one were concurrently present in a given trigger detection region or encoding/sensing region, the objects in the set may nonetheless be distinguishable if they are sufficiently separated in position that only one of them at a time can be in a given trigger detection region or encoding/sensing region; in this case, for example, a trigger detector can provide, for each of a set of distinguishable objects, a respective trigger signal in response to the object when it is in the detector's trigger detection region. Where a distinction between a trigger detector's distinguishable and non-distinguishable objects in a given implementation can be described in terms of a parameter, such as extent of separation of position, the distinction may be referred to as a "resolution limit" of the trigger detector. Different kinds of resolution limits can affect a trigger detector, encoder/sensor, or other sensor: A limit of sensitivity, for example, can prevent a sensor from detecting a thing, i.e. the sensor cannot distinguish the thing from background; a limit on spatial resolution can prevent a sensor from distinguishing similar objects that are not sufficiently separated in position, as described above; and other kinds of limits can prevent a sensor from distinguishing objects that are different, e.g. where objects provide signals but signal strengths are so different that a sensor tuned to sense one cannot concurrently sense another.

In some implementations, detectors or sensors can obtain information about objects by receiving signals from them; for example, signals in the form of light can emanate from an object, whether through emission (e.g. radiation, fluorescence, incandescence, chemoluminescence, bioluminescence, cathodoluminescence, other forms of luminescence, etc.), elastic or inelastic scattering (e.g. reflection, deflection, diffraction, refraction, etc.), or transmission, and can be sensed by a photosensor. The light "emanates from" or is simply "from" the object, and may be referred to herein as "emanating light". An object from which light is emanating may be referred to herein as a "light-emanating object". In other implementations, detectors or sensors can obtain information about objects in other ways, some of which are mentioned herein; in particular, impedance-based sensors can obtain information about objects in various ways, resulting from, for example, interactions between objects and an arrangement of electrodes or an arrangement of Hall effect sensors.

Examples of objects that could occur in implementations as described below include droplets, small volumes of fluid, single molecules, agglomerated molecules, molecule clusters, cells, viruses, bacteria, lengthy polymers such as DNA or protein chains, submolecular complexes such as tags on DNA or protein chains, microparticles, nanoparticles, beads or other small particles that can bind and carry specific chemicals or other analytes, emulsions, any such type of object on a support structure such as a slide or in an array such as an array of sample wells, and a distinguishable region of a surface such as a small area of a sheet of paper or other image-bearing medium; a distinguishable surface region, could, for example, be a colored spot. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be a "scattering component" of a droplet. An analyte (i.e. a chemical species being investigated) in a droplet or other object can act as a fluorescent, absorbent, or scattering component. Analyte that is otherwise homogeneously distributed, for example, can be localized by binding to carrier beads, resulting in a moving object that emanates light or provides other signals in a way that depends on the analyte.

With respect to a light-emanating object, the expressions "characteristic of an object" and "emanating light including information" have related meanings: The term "characteristic" refers to a trait, quality, or property of an object that can be measured and that persists with a given value or within a given range or other subset of possible values while light that "includes information about the characteristic" is emanating from the object. In appropriate implementations, characteristics of an object could include mass, volume, density, cross-section or other shape, chemical composition, position, speed, acceleration, direction of movement, spin axis, directional or angular velocity or momentum, net charge, charge polarity, absorption spectrum, emission spectrum, scattering spectrum, and so forth. Therefore, emanating light "includes" information about a characteristic of an object if information included in the emanating light indicates a value, range, or other measure of the characteristic. Similar terminology can apply to types of interactions other than emanating light and to information of other types that can be included in light emanating from an object or that can be detected or sensed from other types of interactions; some exemplary implementations described herein relate to other types of interactions, such as interactions with impedance-based sensors, and other types of information.

Emanating light or signals resulting from other types of interactions can "include information" in many ways, some of which are described below in relation to specific implementations. Various criteria could be used to determine whether emanating light or a signal resulting from another type of interaction includes specified information, and such criteria can be referred to as "encoding criteria". Some encoding criteria, for example, involve comparison of magnitude of a signal with noise magnitude, e.g. signal-to-noise (S/N) ratios, because S/N ratio can affect whether specified information can be recovered from sensing results obtained by photosensing emanating light. Other types of encoding criteria could be used as appropriate. Where emanating light or a signal resulting from another type of interaction satisfies an appropriate encoding criterion for specified information, the light or signal may be said to "encode" the information.

Similarly, sensing results, whether from photosensing emanating light, from impedance-based sensing (e.g. with electrodes or Hall effect sensors), or from another type of sensing, can "include information" in many ways, and similar encoding criteria could be applied as with signals. Where sensing results indicate one or more time-varying waveforms, the sensing results can be referred to as having "encoded time variation" or as "indicating time variation". As implied above, sensing results that include encoded time variation or other types of encoded information are sometimes referred to herein as "encoded sensing results" to distinguish from sensing results that might not be encoded. If the encoded information results from relative motion of objects, the sensing results or time variation that include the information may be referred herein as "motion-encoded", and the information itself may also be described as "motion-encoded information".

The term "waveform" is used herein in the general sense of any set of values that varies over one or more dimensions, whether continuous or discrete, whether analog or digital, and whether measured or obtained in any other way; a "time-varying waveform" is a waveform that varies over a time dimension. Some of the time-varying waveforms described below in relation to exemplary implementations include intensity values, but the expression "time-varying waveforms" also encompasses other values that vary over time, including purely numerical values with no specified units or other physical significance. A "sensed time-varying waveform" is a time-varying waveform that is indicated by sensing results obtained over time. For example, if a photosensor provides sensed quantities that indicate intensity of received light, its sensing results could indicate a time-varying waveform indicating intensity sensed over time.

In a system in which trigger detection and/or encoding/sensing are performed, an object moves relative to a region or component or feature of the system or "has relative motion" if the object has a succession of positions over time with respect to the region, component, or feature; the succession of positions is sometimes referred to herein as the object's "path", even though the object may not itself be moving in an absolute sense but only relative to the region, component, or feature.

More generally, the term "path" is used herein in the general sense of a series of positions and/or configurations that a relatively moving and/or varying object can have during its relative motion and/or variation. For generality, a part of an object's relative motion, such as a part of a path is sometimes referred to herein as a "segment", which could encompass any continuous series of one or more positions and/or configurations within the relative motion.

An object's relative motion, if it approximates or is similar to a straight, curving line, or other line without sharp angles or other vertex-like changes of direction, is treated herein as providing a directional orientation as follows: A direction parallel or approximately parallel to the motion is sometimes referred to as a "longitudinal" or "lengthwise" direction, while a direction perpendicular or approximately perpendicular to the path is sometimes referred to as a "radial", "lateral", or "transverse" direction. The lengthwise direction in which the object is moving is sometimes referred to as "forward" or "downstream", while the opposite direction is sometimes referred to as "backward" or "upstream". A radial direction away from the object's path is "out" or "outward", while a radial direction toward its path is "in" or "inward". Light propagating toward the path may be referred to as "incoming" or "incident", while light propagating away from the path may be referred to as "outgoing". A component or arrangement of components is "along" the path if it is disposed near the path and has some extent in a longitudinal direction. A component or arrangement of components is "around" the path if, in a plane transverse to the path, it intersects multiple radial directions, at least two of which are separated by approximately 180 degrees of arc. In general, it should be understood that the above directional orientation is arbitrary and only for ease of description, and that an object's relative motion may have any appropriate orientation.

In FIG. 1, relative motion component 16 causes motion of object 20 and other objects (not shown), and the path of object 20 includes several segments, some of which are indicated by arrows 30, 32, and 34: Arrow 30 indicates a segment in which object 20 has relative motion into trigger detection region 22; arrow 32 a segment in which object 20 has relative motion from region 22 into encoding/sensing region 24; and arrow 34 a segment in which object 20 has relative motion within region 24. Arrows 30, 32, and 34 are all shown extending in a longitudinal direction, but this is only illustrative; the segments they indicate could have any appropriate shape and/or direction, as suggested by some of the exemplary implementations described below.

FIG. 1 also illustrates several ways in which circuitry component 18 could respond to the respective trigger signal of object 20. Some of these ways involve circuitry within circuitry component 18 that is illustrated as control circuitry 40, and others involve circuitry illustrated as processing circuitry 42. As suggested by the words "AND/OR" between circuitry 40 and circuitry 42 and as illustrated in relation to exemplary implementations below, a given implementation might include only one or the other of control circuitry 40 and processing circuitry 42 even though the two are not mutually exclusive; furthermore, implementations that include both control circuitry 40 and processing circuitry 42 might include separate circuitry for each of them or might include a microprocessor or other processor or central processing unit (CPU) that is part of both of them, such as by being programmed so that it can operate in both ways when appropriate.

As illustrated by lines 44 and 46 representing control signals from control circuitry 40 and the words "AND/OR" between lines 44 and 46, control circuitry 40 could respond to the trigger signal by providing control signals that cause one or both of encoder/sensor 14 and relative motion component 16 to operate so that encoder/sensor 14 provides encoded sensing results. The encoded sensing results indicate at least one time-varying waveform with information resulting from relative motion of object 20 within region 24, as indicated by arrow 34.

As illustrated by line 48, processing circuitry 42 could respond to the trigger signal by obtaining data from the encoded sensing results. The data indicate at least one time-varying waveform with information resulting from relative motion of object 20 within region 24. Processing circuitry 42 could provide the data for further operations or for storage or transmission, as suggested by line 48.

In any of these cases, information in a time-varying waveform could result from an object's relative motion within an encoding/sensing region in any of various ways, some of which are described below in relation to exemplary implementations. For example, an object could move relative to one or more parts or components of an encoder/sensor or relative to one or more patterns or other features produced within an encoding/sensing region by an encoder/sensor such that information about the object's relative motion, e.g. about relative speed or other relative rate of displacement, can be included in emanating light or in other signals resulting from interaction between the object and the encoder/sensor and can therefore be included in encoded sensing results. An object that has relative motion within an encoding/sensing region is sometimes also referred to herein as "moving" or as having "motion" or "movement", but an object's relative motion within an encoding/sensing region may result from any appropriate motion of the object and/or motion of parts or components of an encoder/sensor or patterns or other features produced within the encoding/sensing region by the encoder/sensor. In other words, relative motion of an object within an encoding/sensing region includes any relative motion between the object and parts or components of an encoder/sensor or patterns or features produced within the encoding/sensing region by the encoder/sensor, such as a pattern of excitation or of filtering or another environmental pattern or feature.

Emanating light that includes information about an object's relative motion within an encoding/sensing region is sometimes referred to herein as "motion-affected" light, as including "motion-dependent information", or as having "motion-dependent encoding". For example, relative motion component 16 could cause relative motion of object 20 by carrying it in fluid, such as liquid, gas, or aerosol, along a path segment within region 24 in which it emanates light that is transmitted and/or reflected by a filter arrangement to include information about the relative motion, thus becoming motion-affected light; in such a case the object may be referred to as being "carried" by fluid. In another example, object 20 could be contained in or otherwise supported by a support structure, and relative motion component 16 could cause scanning, rotation, or other relative motion between the support structure and a filter component or another component such as a photosensor, with object 20 emanating light that is transmitted and/or reflected so that it becomes motion-affected light.

Similarly, encoded sensing results or data that indicate a time-varying waveform with information resulting from an object's relative motion within an encoding/sensing region are also sometimes referred to herein as "motion-affected" sensing results or data, as illustrated by the label adjacent line 48. Motion-affected sensing results and/or data can be used in many ways, some of which are described below in relation to exemplary implementations. For example, motion-affected sensing results or data can be used to obtain data indicating some or all of the encoded information, an operation referred to as a "decoding" operation. The results of decoding can be used to distinguish objects and in various other ways, some of which are described below in relation to exemplary implementations. In exemplary applications, such as where distinguished objects are registration marks in documents or other images, appropriate subsequent operations can be controlled based on results of operations that distinguish objects.

More generally, sensing results are obtained "from" or "in response to" a stimulus such as an object or an object's relative motion if the sensing results result from the stimulus and the sensing results include information about the stimulus, e.g. about one or more characteristics of the object or about the object's relative motion. For example, sensing results can "indicate time-varying waveforms in response to" objects, relative motion of objects, or another stimulus if the sensing results are obtained in response to the stimulus and indicate time-varying waveforms that include information about the stimulus; more specifically, sensing results can indicate time-varying waveforms that "depend on" an object's relative motion within an encoding/sensing region, meaning that the waveforms include encoded information resulting from the object's relative motion within the encoding/sensing region. An encoder/sensor can obtain sensing results in response to an object and/or an object's relative motion in many different ways.

Components of system 10 can be implemented in any appropriate way, and some exemplary implementations are described below. Trigger detector 12, for example, could be a Coulter counter, a Mie scatter sensor receiving a backward- or forward-scattered signal, an array of one or more discrete photosensors, one or more cells of a photosensing array, and so forth; exemplary trigger detection techniques are described in U.S. Pat. No. 7,358,476, entitled "Sensing Photons from Objects in Channels" and incorporated herein by reference in its entirety. Encoder/sensor 14, relative motion component 16, and circuitry component 18 could also take a wide variety of different forms, illustrative examples of which are described below. For example, each of the below-described exemplary implementations involves relative motion within an encoding/sensing region, but relative motion component 16 can cause relative motion in many different ways, producing, for example, one or both of fluidic relative motion and support-based relative motion; additional examples of relative motion techniques are described in co-pending U.S. patent application Ser. No. 12/337,796, entitled "Causing Relative Motion" and incorporated herein by reference in its entirety. In general, encoder/sensor 14 can include any suitable type of sensor such as a photosensor or an impedance-based sensor. Also, encoded sensing results can initially take the form of analog or digital electrical signals, depending on the structure and circuitry included in encoder/sensor 14, but encoded sensing results could be converted to other forms, such as optical or other electromagnetic signals, such as for subsequent storage, transmission, and processing; additional examples of sensing techniques are described in co-pending U.S. patent application Ser. No. 12/337,737, entitled "Obtaining Sensing Results Indicating Time Variation" and incorporated herein by reference in its entirety.

Within circuitry component 18, control circuitry 40 could be implemented in many different ways, ranging from relatively simple connections between trigger detector 12 and encoder/sensor 14 to various complex, processor-based implementations. Processing circuitry 42 requires at least some circuitry capable of using encoded sensing results from encoder/sensor 14 to obtain motion-affected data indicating at least one time-varying waveform with information resulting from relative motion of object 20 within region 24.

Figure 2:
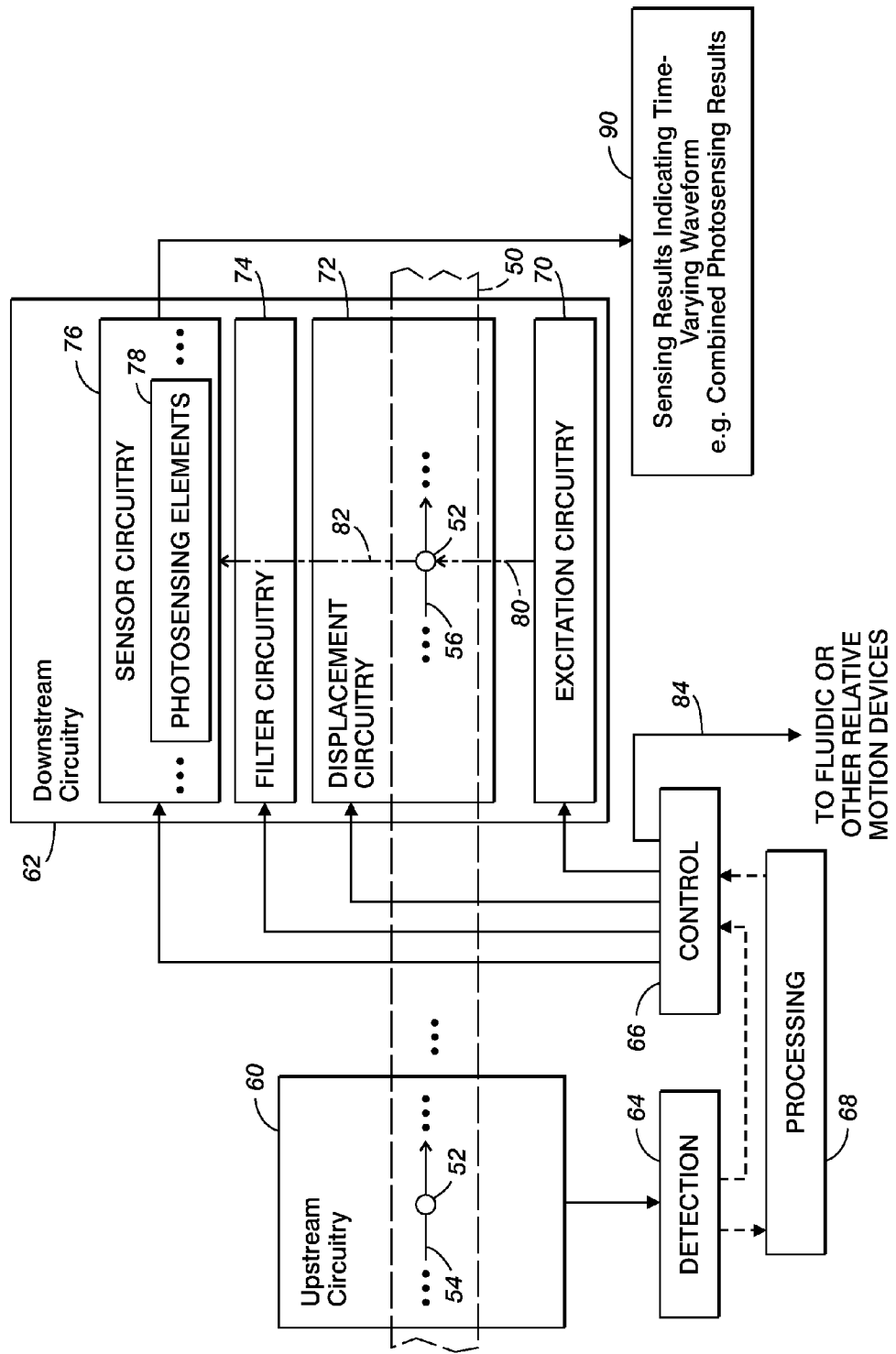
FIG. 2 is a schematic diagram showing general features of implementations of systems as in FIG. 1 in which objects move relative to upstream and downstream circuitry.

In FIG. 2, dashed boundary 50 represents a channel or other region in which objects can have relative motion caused by fluidic or other relative motion devices (not shown). Object 52 is one of a number of distinguishable objects that have relative motion within the region in a downstream direction indicated by arrows 54 and 56. The path of object 52 includes a segment in which it is in a trigger detection region relative to upstream circuitry 60, which operates as a trigger detector, and another segment in which it is in an encoding/sensing region relative to downstream circuitry 62, which operates as an encoder/sensor. During relative motion of object 52 within the encoding/sensing region, control signals cause encoding of information in emanating light.

When object 52 is moved into the trigger detection region, upstream circuitry 60 detects it, an operation that is represented by box 64. In response to detection of object 52, control signals are provided that cause one or both of downstream circuitry 62 and the relative motion devices to operate so that downstream circuitry 62 provides encoded sensing results indicating at least one time-varying waveform with information resulting from relative motion of object 52 within the encoding/sensing region, an operation represented by box 66. Control in box 66 can be performed in response to processing of detection signals from circuitry 60, an operation represented by box 68.

Downstream circuitry 62 could be implemented in many different ways to provide encoded sensing results. FIG. 2 illustrates several different types of circuitry that it could include, though downstream circuitry 62 could also be implemented with any appropriate subset of the types of circuitry shown.

In implementations with all types of circuitry as shown, excitation circuitry 70 can be controlled to provide excitation; displacement circuitry 72 (and possibly also relative motion devices) can be controlled to provide relative displacement of object 52 within region 50; filter circuitry 74 can be controlled to perform filtering, such as on emanating light; and sensor circuitry 76 can be controlled to perform sensing. More specifically, sensor circuitry 76 can include photosensing elements 78, such as in a longitudinal sequence of discrete photosensing elements or a longitudinal sequence of sets of cells in a photosensing array; discrete photosensing elements or sets of cells on ICs with photosensing arrays could have different extents, different colors, or different intensities. A "longitudinal sequence" of photosensing elements or other sensing elements, as used herein, is a sequence that extends in a longitudinal direction as defined above; for example, interactions occurring in each of a sequence of segments of an object's path could be sensed by a respective sensing element in a longitudinal sequence.

In an example suggested by arrows 80 and 82, excitation circuitry 70 provides excitation light represented by arrow 80 and, in response, object 52 provides emanating light represented by arrow 82, which is filtered in response to filter circuitry 74 and sensed by photosensing elements 78. The emanating light could result, for example, from fluorescence of a dye or other "tag" attached to object 52 or from native fluorescence or autofluorescence of object 52 itself, e.g. due to ultraviolet light or other excitation of intrinsic cell material or other material in object 52; except as otherwise noted, however, implementations described herein can additionally or alternatively employ chemofluorescence, biofluorescence, absorption, scattering, or other phenomena that do not require concurrent excitation. More generally, excitation could take any appropriate form and is not limited to illumination, and excitation and emanation need not be concurrent or otherwise coincident, but could have any appropriate relationship in space and time. Some examples of excitation are described below in relation to exemplary implementations.

On the other hand, downstream circuitry 62 may not include all types of circuitry shown in FIG. 2 in other implementations. For example, in some exemplary implementations described below, sensor circuitry 76 includes only an impedance-based sensing device with electrodes, Hall effect sensors, inductors, or other components in an appropriate pattern to provide encoded sensing results when interacting with an object. In such implementations, operations of excitation circuitry 70 and filter circuitry 74 would ordinarily not affect sensing results, and displacement circuitry 72 might also be ineffective in encoding information. In such implementations, one way to encode sensing results with information about an object's relative motion is to provide control signals through line 84 to fluidic or other relative motion devices, so that the relative motion itself varies in a way that encodes information. Another approach in such implementations and in certain other implementations is to operate processing circuitry to obtain data from the sensing results in response to an object's trigger signal; this approach may be appropriate in general where the sensing results are available for sampling and analog-to-digital conversion continuously or almost continuously, making it possible for the processing circuitry to obtain data indicating a time-varying waveform indicating information resulting from the relative motion.

As a result of the controlled operation of one or both of downstream circuitry 62 and relative motion devices (not shown), sensor circuitry 76 provides sensing results indicating one or more time-varying waveforms with information resulting from relative motion of object 52 within the encoding/sensing region, as shown in box 90. More specifically, if photosensing elements 78 include a longitudinal sequence, photosensing results from the sequence could be combined to provide sensing results indicating a time-varying waveform with information resulting from the relative motion.

Figure 3:
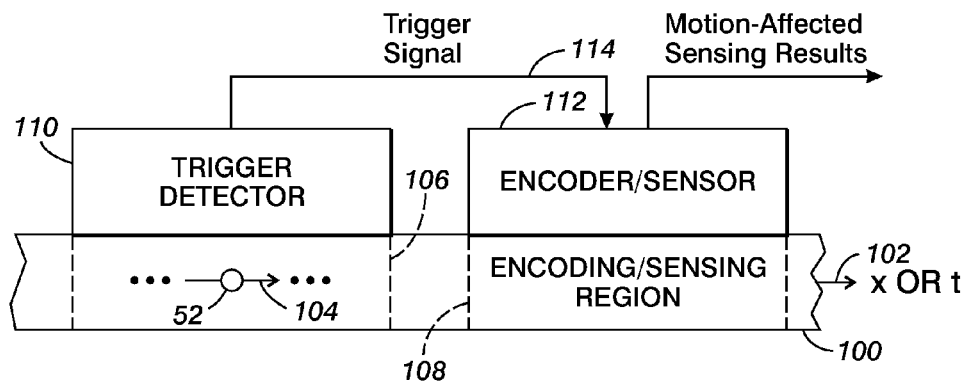
FIG. 3 is a schematic diagram showing features of fluidic implementations of upstream and downstream circuitry as in FIG. 2 in which a trigger detector provides a trigger signal to an encoder/sensor.

FIG. 3 illustrates a more specific example of general features shown in FIG. 2, resembling in ways the implementation in U.S. Pat. No. 7,358,476, entitled "Sensing Photons from Objects in Channels" and incorporated herein by reference in its entirety. Channel 100 is a fluidic channel within which fluid flows in a longitudinal direction indicated by arrow 102, such as in response to one or more fluidic devices such as pumps. As suggested by the label "x OR t" on arrow 102, relative motion of object 52 within channel 100 can be treated either as extending in space, such as along an x-direction, or as occurring over time, t; unless otherwise indicated hereafter in relation to a specific exemplary implementation, the x-direction refers to an object's actual relative motion and therefore might not in some cases follow a straight line relative to the environment. Although the relative speed or other relative rate of displacement of an object may vary, information about its speed or other rate of displacement can be sufficient to allow an approximate mapping between its x-direction positions and times t; more generally, mapping between an object's x-direction positions and times t can be based on any suitable system, such as with trigger detection techniques as described herein and in U.S. Pat. No. 7,358, 476, entitled "Sensing Photons from Objects in Channels", incorporated herein by reference in its entirety, or from other techniques.

Object 52 is carried by the fluid in the longitudinal direction, as indicated by arrow 104. In the illustrated position, object 52 has had relative motion into trigger detection region 106 and will have relative motion from region 106 into encoding/sensing region 108 and then within region 108. As a result of the relative motion of object 52 into region 106, trigger detector 110 provides a respective trigger signal on line 114, which illustratively operates as control circuitry. Encoder/sensor 112 receives the trigger signal as a control signal, causing it to operate so that it provides motion-affected sensing results that indicate at least one time-varying waveform with encoded information resulting from the relative motion of object 52 within region 108.

An implementation as in FIG. 3 may be appropriate, for example, for relatively simple implementations of encoder/sensor 112. For example, if only one component of circuitry in encoder/sensor 112 responds to the trigger signal, no other control signals may be required. Several exemplary implementations similar to FIG. 3 are described below.

Figure 4:
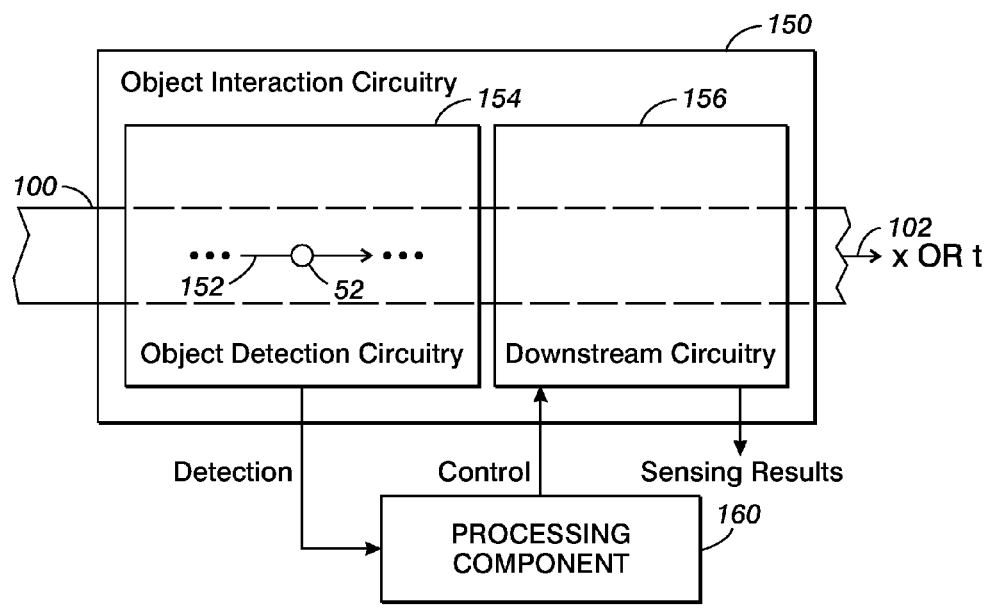
FIG. 4 is a schematic diagram showing features of implementations of upstream and downstream circuitry as in FIG. 2 in which a processing component receives signals from an object detection element and provides control signals to downstream circuitry.

FIG. 4 illustrates a more complex type of implementation in which fluid in channel 100 again flows as indicated by arrow 102, while object 52 has relative motion in relation to object interaction circuitry 150 as indicated by arrow 152. Object interaction circuitry 150 illustratively extends along a portion of channel 100 in the longitudinal direction indicated by arrow 102. Circuitry 150 includes object detection circuitry 154, which is a trigger detector in the sense that it provides signals indicating detection of objects. Object detection circuitry 154 can, however, provide additional signals such as about the mass, size, or other characteristics of an object in its detection region. Circuitry 150 also includes downstream circuitry 156, which is downstream from object detection circuitry 154 and which provides sensing results.

Processing component 160 in FIG. 4 receives the detection signals from object detection circuitry 154, performs suitable processing operations, and provides control signals to downstream circuitry 156 so that the sensing results are encoded and indicate at least one time-varying waveform with information resulting from relative motion of object 52 within an encoding/sensing region of channel 100. Processing component 160 therefore operates as control circuitry.

An implementation as in FIG. 4 would generally be more complex than an implementation as in FIG. 3. A more complex implementation may, however, be appropriate and perhaps even necessary if downstream circuitry 156 includes two or more components of encoding/sensing circuitry of the types illustrated in FIG. 2 or if control signals are provided both to encoding/sensing circuitry as in FIG. 2 and also to a relative motion component such as a pump or other fluidic device. In these cases, it may be necessary to provide synchronized sequences of control signals rather than a single trigger signal as in FIG. 3. Some exemplary implementations similar to FIG. 4 are described below.

Figure 5:
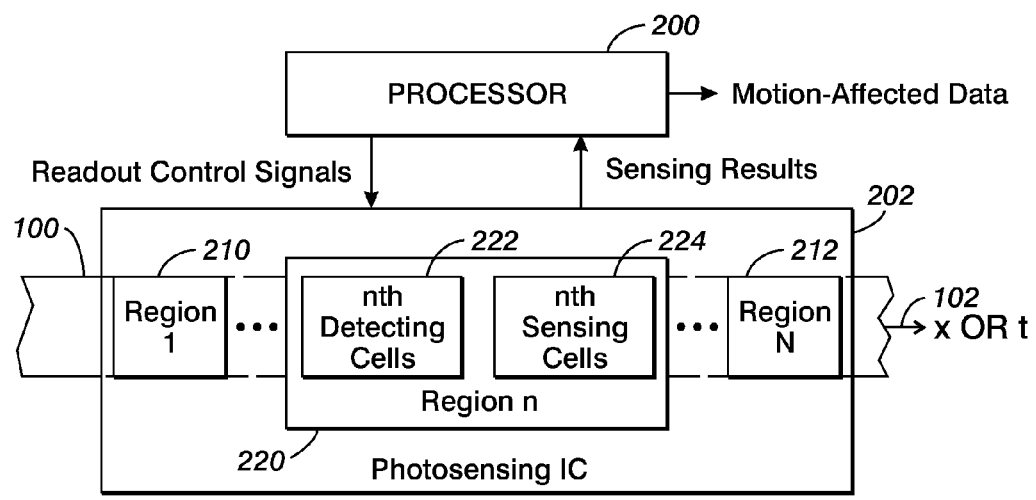
FIG. 5 is a schematic diagram showing features of implementations of upstream and downstream circuitry as in FIG. 2 in which a processor reads out photosensed quantities from a photosensing IC to detect an object and then obtain sensing results.

FIG. 5 illustrates another more complex type of implementation in which fluid in channel 100 again flows as indicated by arrow 102, while a series of distinguishable objects as described above (not shown) have relative motion in relation to circuitry along channel 100. In this type of implementation, processing circuitry, illustratively implemented as processor 200, can read out photosensed quantities from photosensing integrated circuit (IC) 202. The processing circuitry uses some readout quantities to obtain trigger signals and uses others to obtain data indicating time-varying waveforms with information resulting from the relative motion of objects within an encoding/sensing region; the data are therefore labeled as motion-affected data.

In the illustrated example, channel 100 includes N regions 210 through 212, with region 210 being labeled "Region 1" and with region 212 being labeled "Region N." Each of these regions could be configured in any appropriate way, but an exemplary region 220, labeled "Region n," is shown in more detail, with set 222 of photosensing cells labeled "nth Detecting Cells" and with set 224 of photosensing cells labeled "nth Sensing Cells." Processor 200 can provide readout control signals to IC 202 so that cells in set 222 operate as a trigger detector, providing photosensed quantities that serve as or result in a trigger signal when a distinguishable object is in a respective trigger detection region of channel 100. Similarly, processor 200 can provide readout control signals to IC 202 so that cells in set 224, possibly together with other encoding/sensing circuitry as in FIG. 2, provide photosensed quantities that serve as motion-affected sensing results. Accordingly, set 222 can be referred to as a "trigger part" of a photosensing array on IC 202, while set 224, if appropriate, can be referred to as a "sequence part" or a "pattern part" depending on context; trigger parts and pattern parts can be understood from further examples described below, and a "sequence part" refers to a part that includes a sequence of photosensing cells. More specifically, set 224 could include a longitudinal sequence of photosensing cells such that processor 200 or other circuitry, such as on IC 202, can read out and combine photosensed quantities from groups of lines of cells or other subsequences of the cells to provide combined encoded sensing results in accordance with a pattern; in an alternative approach, photosensed quantities from all of the cells in set 224 could be read out and stored, after which they could be combined in accordance with each of a number of patterns to extract different types of information, such as periodic patterns, non-periodic patterns, chirp patterns, and so forth. In an alternative approach, each of regions 210 through 212 could include such a set of cells, with one region's cells being combined in accordance with a periodic pattern, another's in accordance with a non-periodic pattern, another in accordance with a chirp pattern, and so forth.

The technique in FIG. 5 illustrates an example in which control circuitry provides control signals to a trigger detector, in this case readout control signals to cells in set 222. More generally, various control signals could be provided to trigger detectors implemented in a variety of ways. For example, if a trigger detector's sensitivity range can be tuned according to well-known techniques, such as to reduce sensing of background noise, control circuitry could provide control signals to tune sensitivity range; tuning of sensitivity range might also be useful where particles of different signal strength are being sensed concurrently, e.g. a dim particle and a bright particle, to alternate between ranges of signal strength being sensed. Other types of control signals that might be provided to trigger detectors include integration time signals, such as to control sensing periods of photosensing cells, and binning signals, such as to control how photosensed quantities are combined as they are read out of lines of a CCD array or cells of a CMOS array, and various other types of control signals could be used with trigger detectors.

Figure 6:
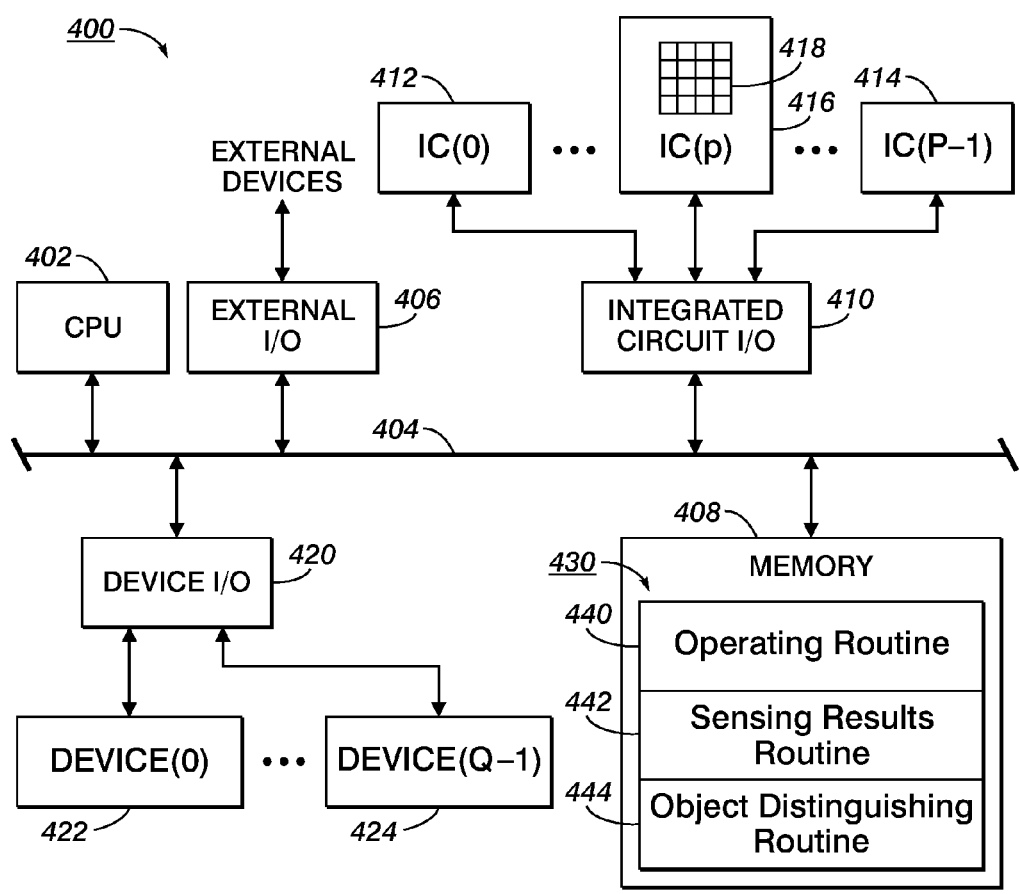
FIG. 6 is a schematic block diagram of a system in which components, such as in any of FIGS. 1-5, can be implemented.

FIG. 6 illustrates system 400, an exemplary system that could implement components as in system 10 in FIG. 1. Although system 400 illustratively includes central processing unit (CPU) 402 connected to various components through bus 404, a wide variety of other architectures could be employed, including any appropriate combination of hardware and software, as well as specialized hardware components such as application specific integrated circuits (ASICs) for one or more of the illustrated components or in place of a software component executed by CPU 402. Furthermore, CPU 402 could be the CPU component of any suitable machine such as a laptop or desktop computer, or could be a specialized computer for system 400, and CPU 402 and other digital components as shown could be replaced by other specialized circuitry, such as an analog signal processor; in a relatively simple application, CPU 402 could be implemented with a single digital signal processor or a CPU of a laptop or other personal computer receiving time-varying signals. On the other hand, in some applications, it may prove advantageous to implement all signal processing with analog circuitry, including operations that compare time-varying waveforms and that obtain their derivatives or other related waveforms, making it possible to replace substantially all the digital components as shown if appropriate.

System 400 also includes external input/output (I/O) component 406 and memory 408, both connected to bus 404. External I/O 406 permits CPU 402 to communicate with devices outside of system 400.

Additional components connected to bus 404 are within or connected to system 400. In the illustrated implementation of system 400, IC I/O 410 is a component that permits CPU 402 to communicate with ICs such as photosensing ICs; M ICs are illustrated in FIG. 6 by a series extending from IC(0) 412 to IC (P-1) 414. ICs 412 through 414 illustratively include IC(p) 416 with a photosensor array 418, which includes photosensing cells. Similarly, device I/O 420 is a component permitting CPU 402 to communicate with various devices in system 400, such as sensing and control devices; Q devices in system 400 are represented in FIG. 6 by device (0) 422 through device (Q-1) 424. In addition to excitation circuitry, displacement circuitry, and filter circuitry as described above in relation to FIG. 2, devices 422 through 424 can include relative motion devices, whether causing fluidic, scanned, rotating, or other relative motion or displacement; for example, devices 422 through 424 could include fluidic devices such as pumps, metering electrodes, smart gates, and other devices for gating and bifurcating, valves, flow or pressure sensors, and so forth. Such fluidic devices could be implemented in various ways; smart gates, for example, could be implemented with MEMS style microgates or by using electromagnetic forces, which are effective because most particles are charged such that an electric field can be used to direct them as desired in a channel.

Memory 408 illustratively includes program memory 430, although instructions for execution by CPU 402 could be provided in various other forms of software or hardware, on or off of CPU 402. The routines stored in program memory 430 illustratively include operating routine 440; sensing results routine 442; and object distinguishing routine 444. In addition, program memory 430 can also store a number of subroutines (not shown) that CPU 402 can call in executing routines 440, 442, and 444.

CPU 402 executes operating routine 440 to operate components of system 400 and, when one of the distinguishable objects enters a trigger detection region, to obtain a trigger signal. In doing so, routine 440 can receive input signals from and provide output signals to devices 422 through 424. For example, to obtain appropriate relative motion of objects, CPU 402 can receive signals from sensors, perform computations to determine what fluidic operations are necessary, and then provide signals to activate pumps, metering electrodes, gates, and valves to produce appropriate relative motion between objects and other components of system 400. CPU 402 can also receive trigger signals from trigger detecting devices or can read out photosensed quantities from a trigger part as suggested in FIG. 5 to obtain trigger signals.

CPU 402 executes sensing results routine 442 to operate components of system 400 in response to a trigger signal, obtaining sensing results and/or data that indicate time-varying waveforms with information resulting from relative motion. In order to do so, CPU 402 can, for example, perform computations to determine what control signals to provide to excitation components, motion devices and other displacement components, filter components, sensing components, or other components or devices in emanating light. In some implementations, CPU 402 can provide control signals to relative motion components to cause motion of objects within encoding/sensing regions, resulting in appropriate encoding. In still other implementations, CPU 402 can respond to a trigger signal by operating to obtain motion-affected data from photosensed or impedance-based sensing results.

In one possible application of system 400, CPU 402 also executes object distinguishing routine 444, such as to obtain data indicating an object's type or other characteristic or, in some applications, to control an operation that selects objects, rejects objects, obtains further information about objects, and so forth. An example of how object distinguishing routine 444 could be implemented is described, for example, in co-pending U.S. patent application Ser. No. 12/022,485, entitled "Obtaining Information from Time Variation of Sensing Results" and incorporated herein by reference in its entirety. Techniques as described herein could be used, however, in various other applications that gather various types of information resulting from relative motion of objects within encoding/sensing regions.

Figure 7:
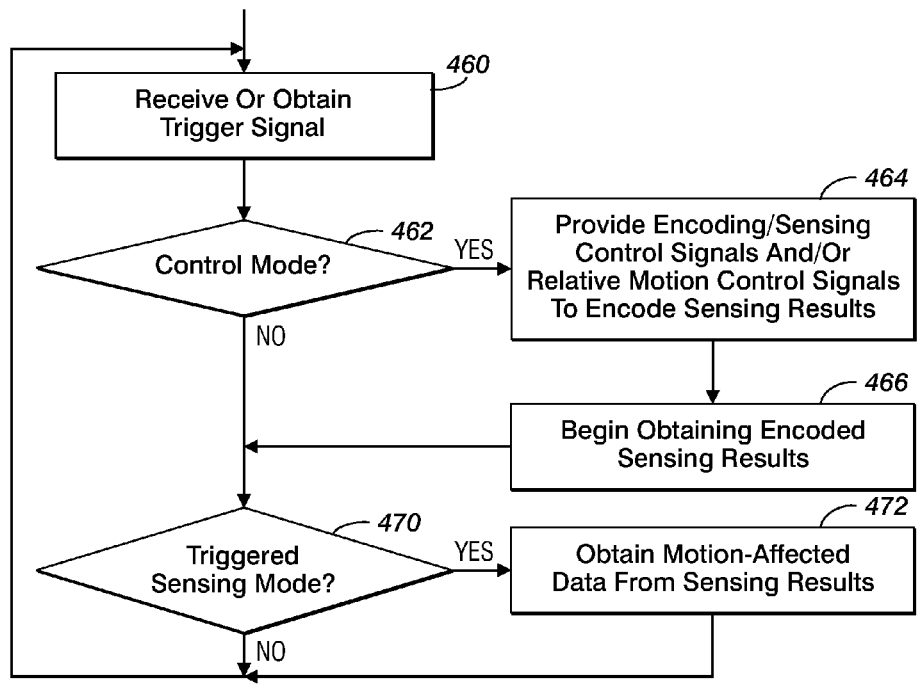
FIG. 7 is a flow chart showing general operations in an implementation of a sensing results routine as in FIG. 6.

Several examples of techniques that can be performed by sensing results routine 442 are described below in relation to exemplary implementations. FIG. 7 illustrates general operations that can be performed by CPU 402 in executing sensing results routine 442 in relatively complex implementations. In simpler implementations a suitable subset of the operations illustrated in FIG. 7 could be performed, and it would also be possible to perform similar operations without a separate CPU or other processor, such as by using other appropriate circuitry to provide signals in response to trigger signals.

The operations in FIG. 7 begin in box 460, in which CPU 402 receives or otherwise obtains a trigger signal indicating detection of a distinguishable object in a trigger detection region. In response, CPU 402 could begin obtaining sensing results, such as by providing readout control signals to one or more of ICs 412 through 414 or by monitoring output from impedance-based sensors or other sensors that provide sensed quantities continuously, whether in analog or digital form.

In reading out photosensed quantities, for example, CPU 402 can perform pre-sensing readout, obtain object information and sensing periods, perform sensing readout with sensing periods and analog adjustment, digitally adjust sensing results and store quantities for an object, and combine the quantities for an object to produce its characteristic data. CPU 402 could, for example, call a subroutine implemented as described in U.S. Pat. No. 7,358,476, entitled "Sensing Photons from Objects in Channels", and 2007/0146704, entitled "Sensing Photon Energies Emanating from Channels or Moving Objects", each of which is incorporated herein by reference in its entirety. Such a subroutine can be implemented for single objects moving past arrays or for spaced multiple objects moving past arrays, provided spacings between objects are sufficient to avoid having more than one object in an encoding/sensing region or other kinds of interference. Also, such a subroutine can follow a general strategy of performing a series of readout operations, after which information for an object is combined and its characteristic data is provided, although it would also be possible to provide the information from each readout operation immediately.

In any case, CPU 402 then makes certain modifications in its sensing operations in order to obtain motion-affected sensing results and/or data. These modifications are illustrated in FIG. 7 in terms of two types of modes, either or both of which can be applicable at a given time. In general, however, the operations in FIG. 7 can be operated without explicit modes, and further without explicitly testing to determine whether a given mode applies—for example, CPU 402 could always operate as if it was in one or both of the modes.

The first mode is referred to as the "control mode"; when CPU 402 is in the control mode, it provides control signals in response to a trigger signal, and the control signals cause encoding/sensing and/or relative motion such that the sensing results are encoded to indicate time-varying waveforms with information resulting from relative motion. Therefore, when CPU 402 is operating in control mode, a branch is taken from box 462 to box 464. The operation in box 464 provides encoding/sensing control signals and/or relative motion control signals so that the sensing results are encoded. After the operation in box 464, CPU 402 begins to obtain encoded sensing results, in accordance with the control signals provided in box 464, as illustrated by box 466.

The second mode is the triggered sensing mode, and CPU 402 can operate in the triggered sensing mode whether or not it is also operating in the control mode, depending on other features of an implementation. If operating in the triggered sensing mode, CPU 402 follows the branch from box 470 to box 472. In box 472, CPU 402 operates to obtain motion-affected data from sensing results. If, for example, CPU 402 is obtaining encoded sensing results as in box 466, it can implement the operation in box 472 by obtaining data from the encoded sensing results in a way that preserves information resulting from relative motion. On the other hand, if CPU 402 is not operating in the control mode, it may nonetheless be able to obtain motion-affected data in one of the ways described below, such as with impedance-based sensing; in these cases, the sensing results might, for example, be inherently encoded without the need for control signals as in box 464, so that CPU 402 can obtain data in a way that preserves the inherently encoded information resulting from relative motion without providing control signals as such.

After the operations in FIG. 7 have obtained motion-affected sensing results and/or data in response to a trigger signal, CPU 402 can return and await another trigger signal in box 460, as suggested by the arrows from boxes 470 and 472 returning to box 460. In more sophisticated implementations, CPU 402 could perform operations similar to those in FIG. 7 concurrently for several different trigger detectors, each with a respective encoder/sensor.

Figure 8:
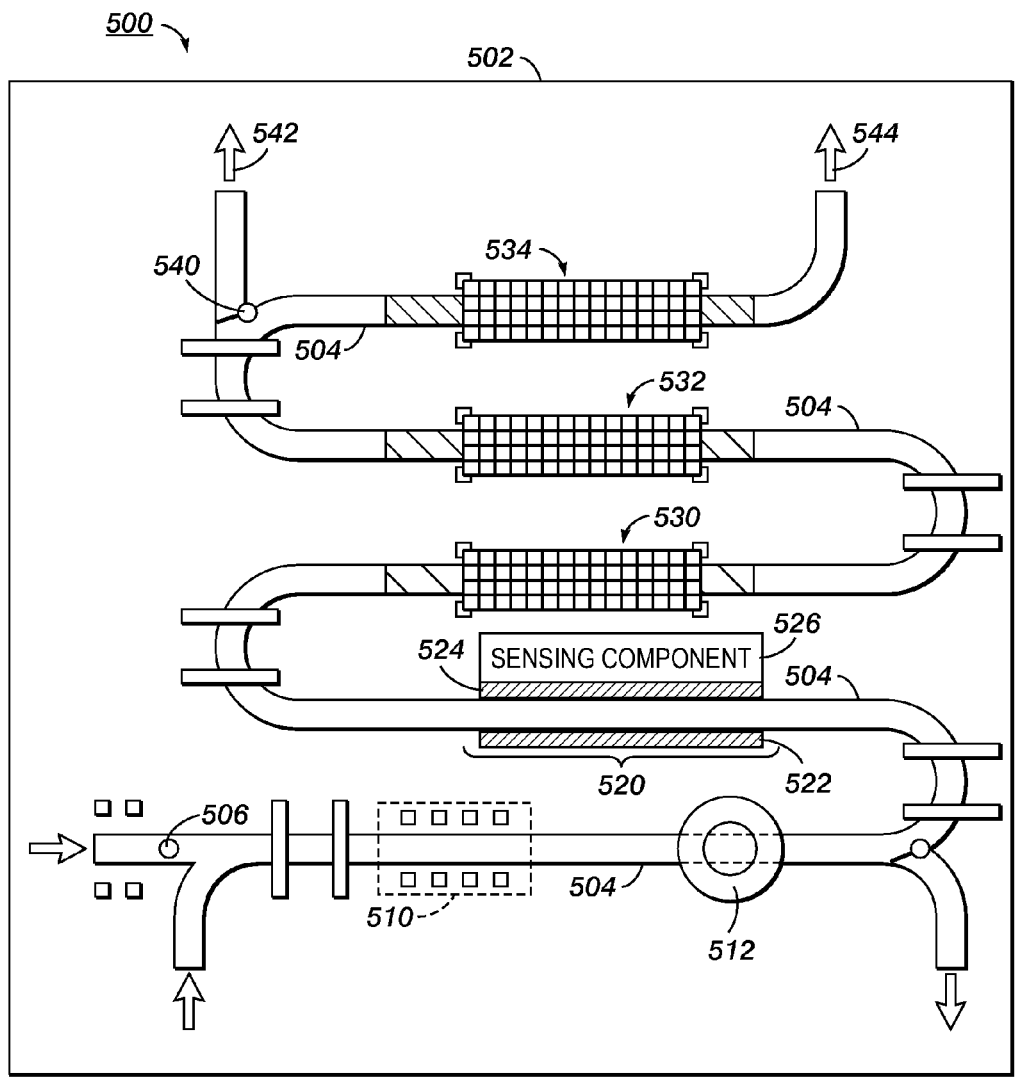
FIG. 8 is a schematic diagram of an analyzer in a fluidic structure, where the analyzer can include a system that can be implemented as in FIGS. 6 and 7.

FIG. 8 illustrates an application of a system as in FIGS. 6 and 7 in analyzer 500 on support structure 502, a fluidic structure. Defined in support structure 502 is serpentine channel 504 through which object 506 can have relative motion, carried by fluid such as liquid, gas, or aerosol or moved in some other appropriate way. Object 506 can, for example, be a biological cell or another object of any of the types mentioned above.

The manner in which object 506 enters channel 504 and is carried by fluid can be the same as described in U.S. Pat. No. 7,358,476, entitled "Sensing Photons from Objects in Channels", and 2007/0146704, entitled "Sensing Photon Energies Emanating from Channels or Moving Objects", each of which is incorporated herein by reference in its entirety. As explained there, object 506 can be carried through channel 504 by operation of propulsion components and can be purged or otherwise caused to exit, together with fluid that is carrying it, from one of several outlets, such as through toggling of valves. While in channel 504, object 506 can have relative motion within interaction regions relative to a series of object interaction components, each of which can obtain information about object 506.

The first two interaction components after object 506 enters channel 504 are illustratively Coulter counter 510, an electrically based particle size detector, and Mie scatter sensor 512, also a particle size detector. Information about size of object 506 from Coulter counter 510 and Mie scatter sensor 512 can be used in obtaining information about its other characteristics. Various other techniques could also be used to obtain particle size information, including techniques that use chirped filter patterns, random filter patterns with small feature size, staircase periodic filter patterns, and so forth, and such techniques could make it unnecessary to use specialized components to determine particle size.

The next interaction component along channel 504 is object interaction component 520, shown schematically in a cross-sectional view along an axis similar to the x OR t axis in FIGS. 3-5, although it would typically be implemented instead with components above and below channel 504, similarly to other object interaction components described below. The schematic illustration of component 520 illustratively includes excitation/displacement component 522, filter component 524, and sensing component 526, all of which might be implemented in a variety of ways, including some of those described above and below; one or more of components 522, 524, and 526 could be omitted or replaced in specific implementations. In addition, component 520 could include a displacement control arrangement with shaped boundaries and/or a motion device or other displacement component (not shown) implemented in one of the ways described above or below.

After passing through component 520, object 506 could be characterized without obtaining further information, or, as in the illustrated implementation, object 506 can continue through subsequent object interaction components, illustratively including components 530, 532, and 534. These could, for example, include first and second fluorescence sensing components and a Raman scatter sensing component. Information obtained from any combination of the object interaction components can be used to distinguish between types of objects, such as different types of biological cells, or to distinguish objects from environment or background. Based on such a distinction, valve 540 at a bifurcation junction can be toggled between two positions, with object 506 exiting as indicating by arrow 542 if valve 540 is in one position and exiting as indicated by arrow 544 if valve 540 is in another position.

The fluidic implementation in FIG. 8 is merely illustrative of a wide variety of implementations of the techniques described herein. For example, any appropriate fluidic or nonfluidic techniques could be used with a wide variety of different types of objects and various types of relative motion to obtain various types of motion-affected sensing results or data.

Figure 9:
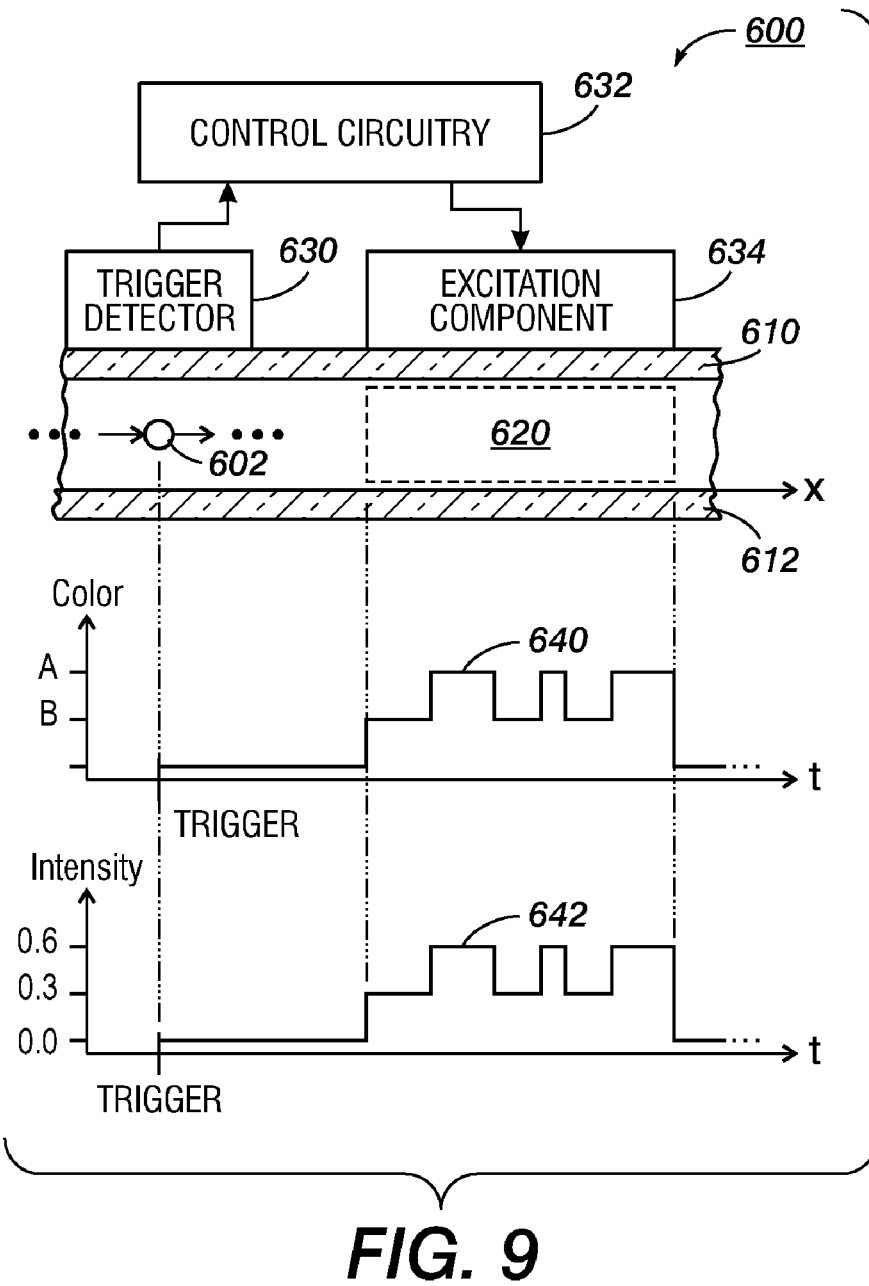
FIG. 9 is a partially schematic cross-sectional view of a system that could be implemented as in FIGS. 6 and 7 and in which control signals are provided to an excitation component, together with graphs showing excitation as a function of time for exemplary types of excitation.

FIG. 9 illustrates system 600 in which time-varying signals, a type of motion-affected sensing results, can be produced by providing control signals to excitation circuitry. As object 602 has relative motion by laminar flow through the channel between wall-like parts 610 and 612, excitation component 634 is able to produce a sequence of different colors in encoding/sensing region 620. As object 602 has relative motion into a trigger detection region of trigger detector 630, detector 630 provides a trigger signal to control circuitry 632, which can then provide appropriate control signals to excitation component 634, such as in one of the ways described above. With appropriate spacing and relative motion of a series of objects such as object 602, each object can receive, after its respective trigger signal from detector 630, substantially the same excitation sequence during its relative motion within region 620.

Curve 640 in FIG. 9 illustrates one example of how the color of excitation in region 620 could vary over time, analogous to techniques for varying illumination in a recreational setting such as a dance hall. As shown, excitation of colors A and B alternates, and is provided for random durations, although it could be provided in a periodic or chirp pattern rather than in a random pattern as shown. Colors A and B could be non-binary excitation spectra, or could alternatively be black and white. Also, the illustrated technique could excite with more than two different colors.

Curve 642 illustrates another example, in which excitation varies between intermediate intensities, such as gray levels, illustratively labeled 0.3 and 0.6 to indicate that they are between minimum intensity of zero and maximum intensity of 1.0. Different intermediate intensities could be provided in this manner with a single light source that can be abruptly switched between intensity levels.

Additional details about an implementation as in FIG. 9 are described in co-pending U.S. application Ser. No. 12/023, 436, entitled "Producing Time Variation in Emanating Light" and incorporated herein by reference in its entirety.

Figure 10:
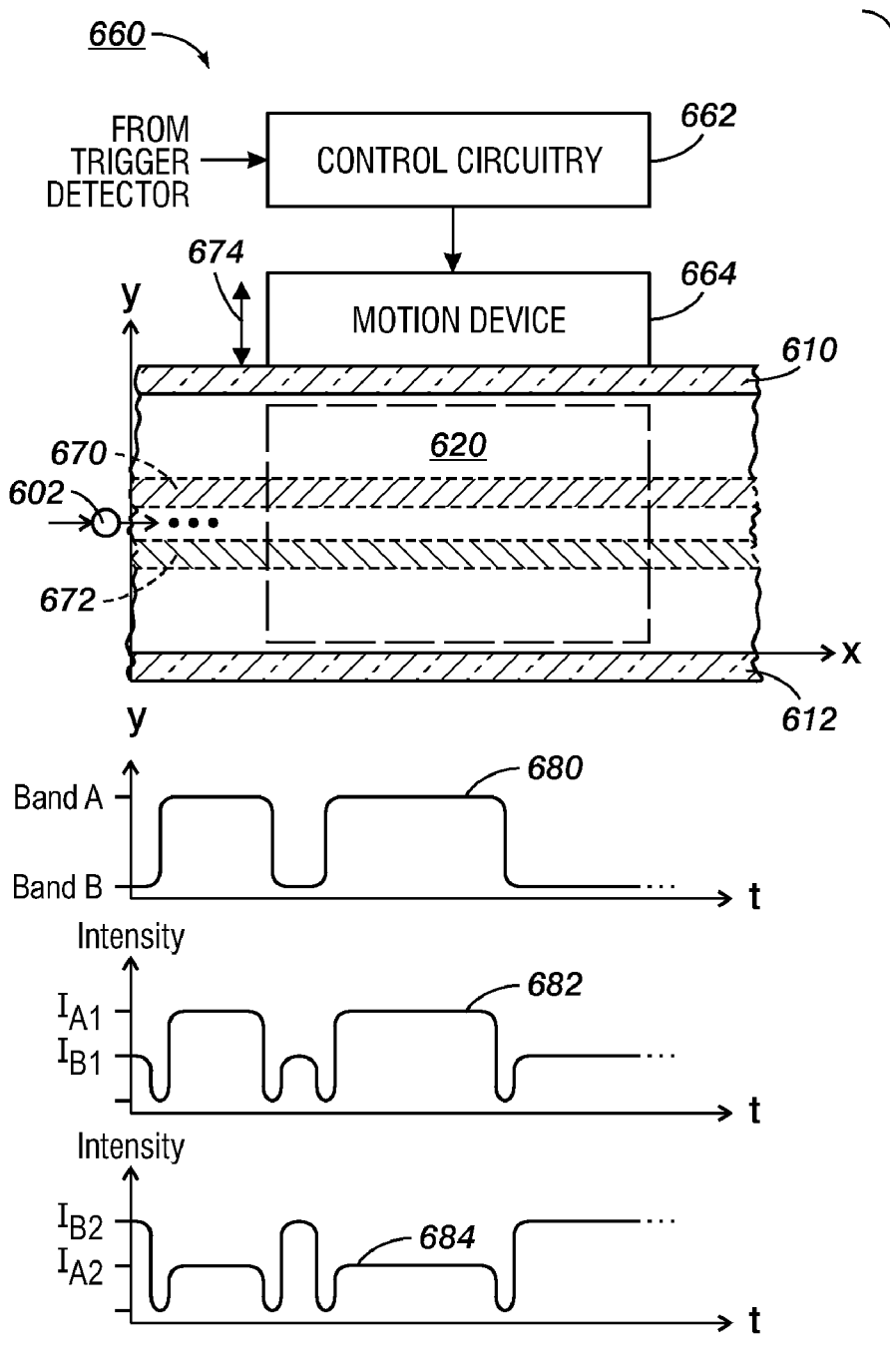
FIG. 10 is a partially schematic cross-sectional view of a system that could be implemented as in FIGS. 6 and 7 and in which control signals are provided to a motion device to produce displacement, together with a graph showing displacement as a function of time and graphs showing sensing results as a function of time for exemplary types of objects.

FIG. 10 illustrates system 660, in which time-varying signals, another type of motion-affected sensing results, can be produced by providing control signals to a motion device or other displacement circuitry. As in FIG. 9, wall-like parts 610 and 612 in FIG. 10 are substantially straight and parallel. Between them are homogeneous longitudinal regions 670 and 672, each extending in the longitudinal direction across encoding/sensing region 620. Regions 670 and 672 could, for example, be excitation regions as described in co-pending U.S. patent application Ser. No. 12/023,436, entitled "Producing Time Variation in Emanating Light" and incorporated herein by reference; stripe-like filter elements as described in co-pending U.S. patent application Ser. No. 12/024,490, entitled "Transmitting/Reflecting Emanating Light with Time Variation" and incorporated herein by reference; or other types of regions such as discrete photosensing elements or parts of a photosensing array.

Motion device 664, which could be an electrically controlled device such as a solenoid or motor-driven piston, produces lateral relative motion between object 602 and regions 670 and 672, as indicated by bi-directional arrow 674. Control circuitry 662 provides signals to control operation of motion device 664 in response to trigger signals from a trigger detector, such as in one of the ways described above. The resulting motion need not be periodic, but could take any appropriate pattern, resulting in arbitrary time-varying signals with features indicating different types of objects. An alternative would be to move the light sources or other components that control positions of regions 670 and 672; more generally, any combination of relative motions between walls 610 and 612 on the one hand and regions 670 and 672 on the other could produce movement as indicated by bi-directional arrow 674. Furthermore, additional variations could be produced by changing fluid flow within the channel so that the speed or other displacement of object 602 changes as a function of time relative to the other movements.

Curve 680 illustrates movement of object 602 in the y-direction between region 670, labeled "Band A", and region 672, labeled "Band B". As illustrated, object 602 spends different lengths of time in each region and can spend a random amount of time in each region, resulting in a random excitation pattern. Curves 682 and 684 illustrate exemplary time-varying signals that could be produced by the technique of FIG. 10 if regions 670 and 672 provide excitation in Band A and Band B, respectively. One type of object responds more strongly to color A in region 670, as illustrated by curve 682, while the other responds more strongly to the color B in region 670, as illustrated by curve 684. As each object has relative motion between regions 670 and 672, it passes through the gap between them, resulting in a brief interruption of the emanating light, so that each curve goes briefly to 0. In curve 682, the intensity in region 670 is I(A1), while the intensity in region 672 is I(B1), a lower value. Conversely, curve 684 illustrates that the intensity is higher in region 672, at intensity I(B2), and lower in region 670, at intensity I(A2). The two curves are, in general, complementary, except for times when they are passing through the gap between regions 670 and 672; object 602 can be moved instantaneously between Band A and Band B, moving very quickly across the gap between regions 670 and 672, so that the times in which it is passing through the gap are very brief.

Figure 11:
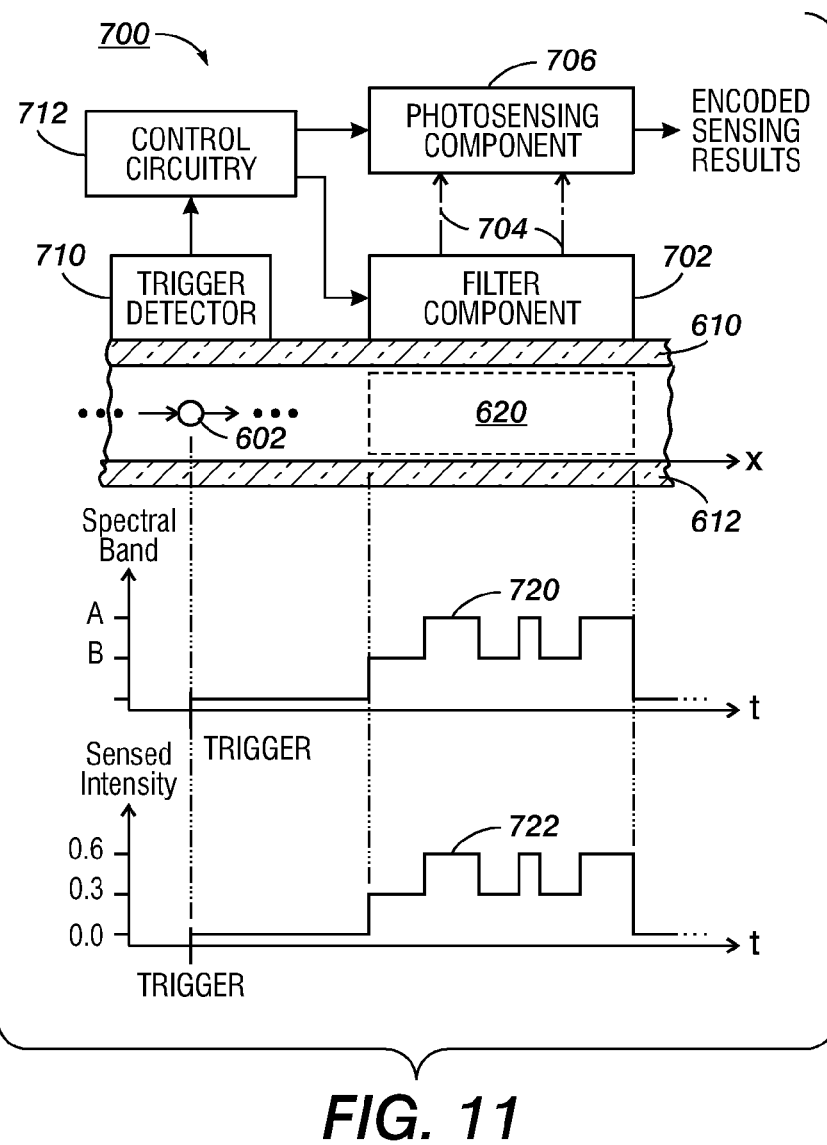
FIG. 11 is a partially schematic cross-sectional view of a system that could be implemented as in FIGS. 6 and 7 and in which control signals are provided to one or both of a filter component and a photosensing component, together with graphs showing exemplary sensing results as a function of time.

FIG. 11 illustrates system 700 in which time-varying signals can be produced by providing control signals to filter circuitry such as a liquid crystal display (LCD) filter and to photosensing circuitry such as discrete photosensing devices and/or photosensing ICs. As object 602 has relative motion by laminar flow through the channel between wall-like parts 610 and 612, filter component 702 receives light emanating from object 602, and provides output light in response, as illustrated by light rays 704. Photosensing component 706 receives at least part of the output light and, in response, provides sensing results. As described in co-pending U.S. patent application Ser. No. 12/024,490 ("the '490 application), entitled "Transmitting/Reflecting Emanating Light with Time Variation" and incorporated herein by reference in its entirety, sensing results from component 706 could be encoded based on a pattern within filter component 702, and sensing results could also be encoded based on a pattern of photosensing elements within photosensing component 706, as illustrated by some of the examples described below. In general, photosensing component 706 could be implemented to include any appropriate arrangement of discrete photosensing elements and/or ICs with photosensing arrays in combination with filter component 702, and some examples of suitable photosensing components are shown and described in the '490 application and elsewhere herein.

Alternatively, or in addition to encoding due to patterns within components 702 and 706, sensing results from component 706 could be encoded in response to a trigger signal from trigger detector 710. As object 602 has relative motion into a trigger detection region of trigger detector 710, detector 710 provides a trigger signal to control circuitry 712, precisely indicating position of object 602 at the time of the trigger signal. Control circuitry 712 can then provide appropriately timed control signals to filter component 702 and photosensing component 706 based on position of object 602, such as signals to provide a sequence of spectral filter bands or signals to perform a sequence of photosensing operations in accordance with a sensing pattern or in one of the other ways described herein.

Curve 720 in FIG. 11 illustrates one example of how sensing results could vary over time due to spectral-dependence of one or both of filter component 702 and photosensing component 706, so that one or more photosensing elements in component 706 respond strongly to a spectral band labeled as "A" and others respond strongly to a spectral band labeled as "B"; the spectral dependence could result from changes in the spectral transmission band of filter component 702 and/or from changes in the spectral photosensing band of photosensing component 706. As shown, strong responses to bands "A" and "B" alternate in a random sensing pattern, although strong responses could instead alternate in a periodic or chirp pattern rather than in a random pattern as shown, and responses could be read out in any appropriate pattern if component 706 is IC-implemented. In general, bands A and B could be non-binary spectral bands, or could alternatively be black and white, in which case one band is broadband (white) and the other is off (black). Also, the illustrated technique could be implemented with more than two different spectral bands.

Curve 722 illustrates another example, in which sensing results vary over time due to intensity-dependence of the combination of components 702 and 706, with some sensing elements in component 706 having greater sensed intensity levels than others due to one or both of time variation in filter component 702 and photosensing component 706 in response to control signals from control circuitry 712. The resulting photosensed quantities have intermediate magnitude levels, such as gray levels, illustratively labeled 0.3 and 0.6 to indicate that they are between minimum sensed intensity of zero (i.e., black or off) and maximum sensed intensity of 1.0 (i.e., white or on). Different intermediate sensed intensities could be provided in a similar manner with other intermediate sensed intensity levels. Also, component 702 could be abruptly or gradually switched between spectral bands or intensity levels as appropriate.

In general, accuracy of the techniques of FIGS. 9-11 depends on obtaining trigger signals that accurately indicate position of object 602, such as from a Coulter counter or from a backward- or forward-scattered signal, so that time variations are correlated to object positions that result in encoded sensing results; accuracy can also depend on the presence of only one object in encoding/sensing region 620 at any given time. Trigger signals can provide additional information about object 602, such as particle size, and this information can be used by control circuitry 632, 662, and 712 to select appropriate control signals to be provided, such as to optimize information encoded in sensing results; for example, if photosensing component 706 includes an IC with a photosensing array, control circuitry 712 could scale the longitudinal widths of sensing pattern stripes that are combined to obtain sensing results, based on the dimension of object 602.

Figure 12:
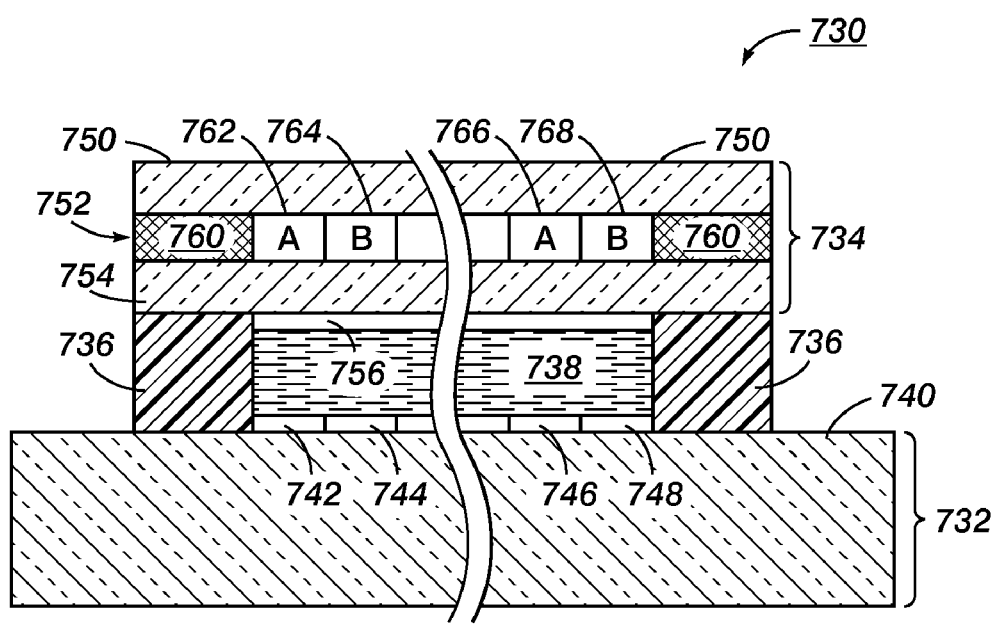
FIG. 12 is a partially schematic cross-sectional view of a liquid crystal display (LCD) filter component that could be used in a system as in FIG. 11.

FIG. 12 illustrates an example of a two-color switchable filter component that could be used to implement system 700 as described above. The techniques in FIG. 12 are based on those described in U.S. Pat. No. 5,491,347, entitled "Thin-Film Structure with Dense Array of Binary Control Units for Presenting Images" and incorporated herein by reference. Techniques as in FIG. 12 could be modified and extended in various ways to obtain multi-color, binary, or gray level filter components.

Filter component 730 includes active matrix structure 732, cover sheet structure 734, spaces 736, and liquid crystal material 738 enclosed in a container defined by structures 732 and 734 and spacers 736. Active matrix structure 732 and cover sheet structure 734 are similar to counterpart structures used in active matrix liquid crystal displays (AMLCDs), and spacer 736 and liquid crystal material 738 can be implemented with currently available or hereafter developed techniques.

Active matrix structure 732 is shown schematically, with substrate 740 and exemplary binary control units 742, 744, 746, and 748. Each of the binary control units 742 through 748 can be switched between its ON and OFF states by driver circuitry (not shown) that can also be on substrate 740 or can be on, for example, an adjacent structure connected with circuitry on substrate 740 through wirebonds or other appropriate structures.

Cover sheet structure 734 similarly includes substrate 750, filter layer 752, passivation layer 754, and electrode 756. Passivation layer 754 can, for example, include clear polyimide, while electrode 756 can be a patterned layer that includes indium tin oxide (ITO), for example. Filter layer 752 can be a mosaic of parts in a pattern in which surrounding area 760 is black or otherwise opaque, while each of filter parts 762, 764, 766, and 768 transmits either spectral band A or spectral band B, as shown. Each of filter parts 762 through 768 is aligned with one of binary control units 742 through 748, so that filter component 730 can be switched between transmitting only band A and transmitting only band B by turning on and off appropriate combinations of binary control units.

The example illustrated in FIG. 12 is only illustrative, and various other techniques could be used to provide filter components that can be electrically controlled. For example, liquid crystal techniques could be used to provide grayscale filtering at different intensities or to provide multi-color filtering with three or more different colors. Various other types of filter components could also be implemented.

Figure 13:
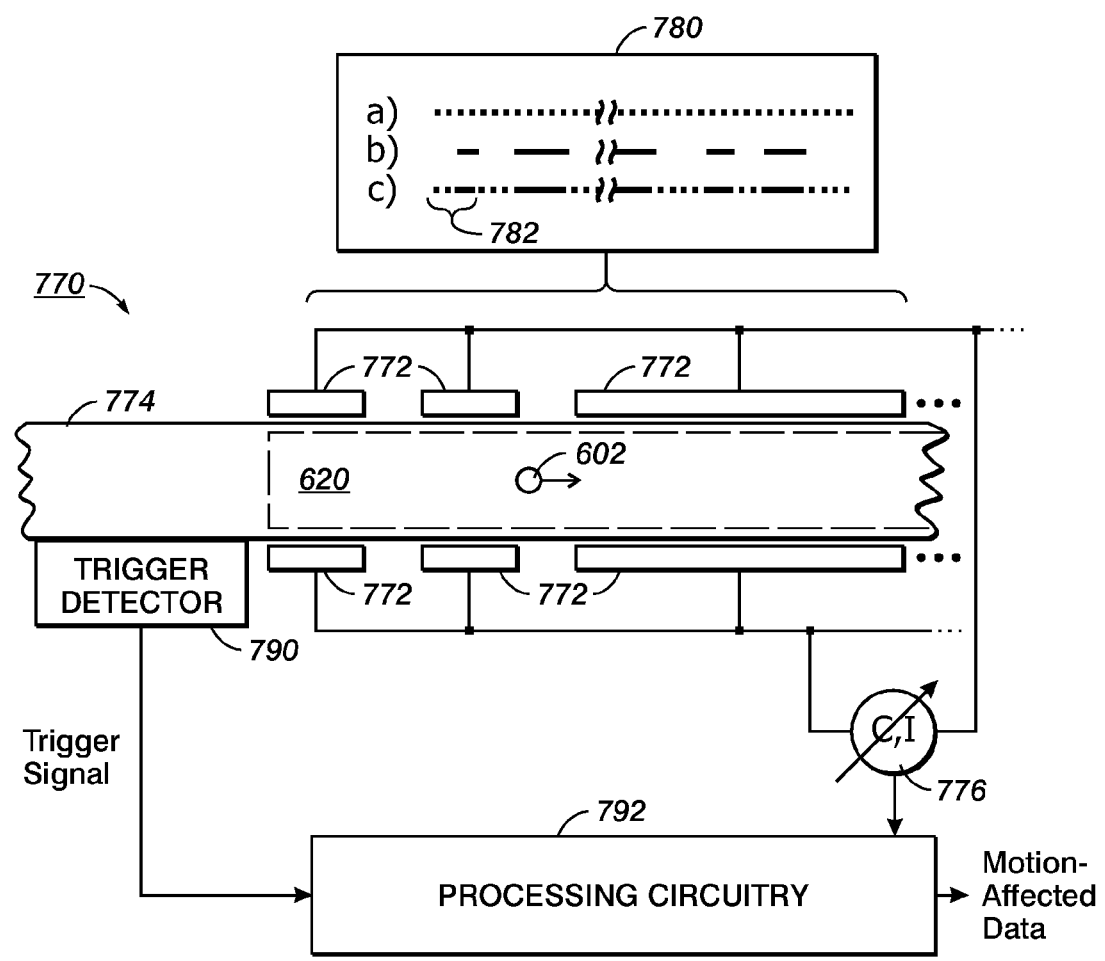
FIG. 13 is a partially schematic cross-sectional view of an impedance-based encoder/sensor that can be included in a system as in FIG. 6.

FIG. 13 shows an example of a non-optical impedance-based sensing pattern technique that can be used to obtain motion-affected data that indicate one or more time-varying waveforms. The technique illustrated in FIG. 13 is similar to a technique described in co-pending U.S. patent application Ser. No. 11/698,409, entitled "Method and System Implementing Spatially Modulated Excitation or Emission for Particle Characterization with Enhanced Sensitivity", incorporated herein by reference in its entirety. Impedance spectroscopy flow cytometry is further described in Cheung, K., Gawad, S., and Renaud, P., "Impedance Spectroscopy Flow Cytometry: On-Chip Label-Free Cell Differentiation", Cytometry Part A, Vol. 65A, 2005, pp. 124-132, also incorporated herein by reference.

Encoder/sensor 770 in FIG. 13 includes an array of electrodes 772 along walls of channel 774, within which object 602 can have relative motion, such as by being carried by a fluid. Electrodes 772 are connected to measurement device 776, which could be implemented as described in the Cheung, et al. article cited above. As suggested, device 776 could provide a time dependent signal such as a measure of capacitance or current, or any other impedance-related electrical or magnetic characteristic that can vary between electrodes on opposite sides of channel 774 or that can be sensed by other similar impedance-based sensors on one or both sides of channel 774. As object 602 has relative motion through channel 774 between electrodes 772 on either side, in other words, device 776 obtains a sensed time-varying waveform indicating a characteristic of object 602.

Although capacitance and conductance are illustratively shown in FIG. 13, a wide variety of different electrical and/or magnetic characteristics could be measured, providing information about a variety of characteristics such as, for a biological cell, cell size, membrane capacity, cytoplasm conductivity, cytoplasm permittivity, and so forth. In particular, electrodes 772 could be replaced with an implementation of Hall effect sensors in a similar pattern to provide impedance-based sensing of magnetic characteristics. Furthermore, device 776 can provide an electrical wobble frequency to electrodes 772 to determine frequency at which a given characteristic is measured by encoding the time-varying waveform.

Electrodes 772 form a pattern that can be understood from the binary signals in box 780. The upper signal, labeled "a)", is a simple periodic binary signal; the middle signal, labeled "b)", is a random binary signal, with varying ON and OFF durations; and the lower signal, labeled "c)" can be obtained by logically combining signals like a) and b) in an alignment similar to that shown—in the illustrated example, the logical combination is an OR operation, so that a given point of signal c) is ON (black) when one or both of the aligned points of a) and b) is ON, but is OFF (white) whenever neither of the aligned points of a) and b) is ON. The positions and lengths of electrodes 772 are proportional to the lengths of ON segments of the binary signal c), and therefore concurrently encode the sensed time-varying wave form both periodically according to signal a) and randomly according to signal b); the proportionality of ON segments of c) with electrodes 772 can be seen by comparing lengths of the first three ON segments of signal c), reference number 782, with lengths of the three upper electrodes 772. As a result of the concurrent encoding described above, information can be extracted from the sensed time-varying waveform, such as about position, speed, and other characteristics of object 602.

The arrangement of electrodes 772 in FIG. 13 is merely illustrative, and could be varied in many ways. For example, electrodes 772 could form a similar pattern along only one side of channel 774 with no electrodes on the other side or with a single, large unpatterned electrode on the other side. Similarly, rather than only being opposite each other, electrodes could be positioned around a channel. Furthermore, different materials could be used for different electrodes and electrodes could be spaced at different distances from the walls of channel 774 in order to obtain more complicated patterns and therefore encode additional information. In general, electrodes 772 could be implemented in various ways, including as a non-periodic arrangement of structured electrodes. Also, simpler binary signals as in box 780 could be combined in any appropriate logical combination other than the OR combination, as appropriate in a given application.

The general technique illustrated in FIG. 13 could also be applied in other contexts. For example, a superposition sensing pattern as illustrated in box 780 could be implemented with Hall effect sensors along one side of channel 774 or in other appropriate arrangements on both sides or around channel 774; also, the pattern could be implemented with photosensing elements in ways described above, such as with discrete photosensing elements with extents as shown or a filter arrangement having a similar pattern. It should be noted, however, that impedance-based sensing elements generally do not perform remote sensing effectively in the way photosensors, acoustic sensors, and certain other types of signal sensors can, so that constraints on positioning are greater for impedance-based sensing elements.

FIG. 13 also illustrates trigger detector 790 along channel 774 upstream from encoder/sensor 770. When object 602 has relative motion into its trigger detection region, trigger detector 790 provides a respective trigger signal to processing circuitry 792. In response, processing circuitry 792 can perform appropriate operations on the signals from measurement device 776 to obtain motion-affected data; more specifically, processing circuitry 792 can obtain data indicating at least one time-varying waveform with information resulting from relative motion of object 602 within encoding/sensing region 620. Note, however, that trigger detection is not necessary for operation of encoder/sensor 770, because the sensing pattern provides a time-modulated signal without triggering; on the other hand, triggering can increase sensitivity by indicating when signal changes will occur and can also reduce power use in situations in which excitation can be switched on and off for each object.

Figure 14:
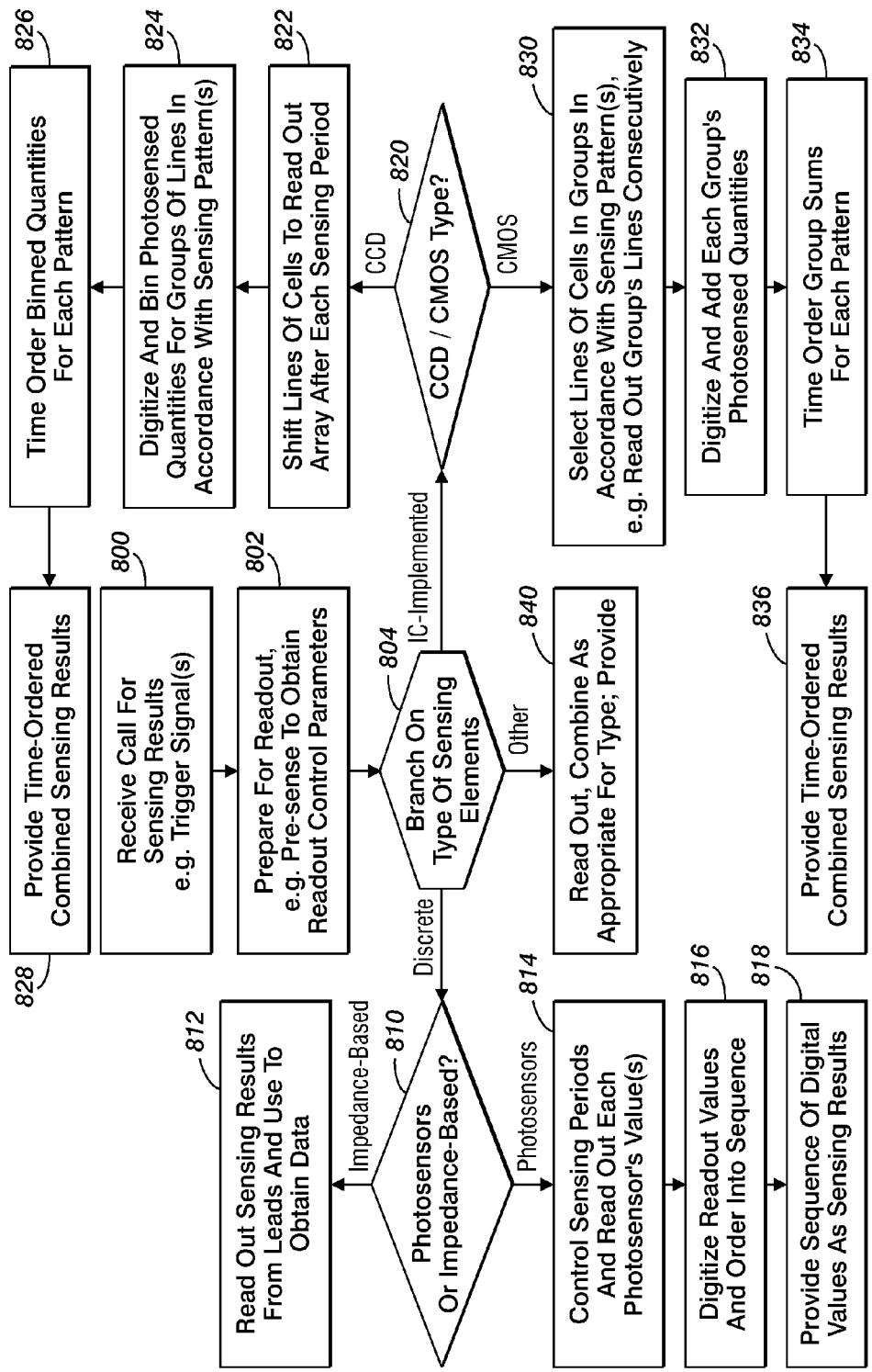
FIG. 14 is a flow chart showing features in exemplary implementations of a sensing results routine as in FIG. 6 for a variety of different types of encoder/sensors.

FIG. 14 illustrates features in exemplary implementations of sensing results routine 442 (FIG. 6), in addition to general features as in FIG. 7. Operations as in FIG. 14 could be implemented for a variety of different types of encoder/sensors, with sensing elements in a variety of arrangements, including arrangements like those above and other arrangements that include, for example, discrete photosensing elements, impedance-based sensing elements such as electrodes and Hall effect sensors, and IC-implemented sensing elements. Techniques as in FIG. 14 are not limited to fluidic relative motion as described above, but could be used with other types of relative motion, some of which are described below.

The implementation of FIG. 14 begins with the operation in box 800 receiving a call to perform operations to obtain sensing results. As suggested in box 800, this call could result from a trigger signal received from trigger detector circuitry, as in implementations in which sensing results operations are performed separately for each of a series of distinguishable objects that have relative motion into a trigger detection region of a trigger detector upstream from an encoder/sensor. In other types of implementations, the call received in box 800 could depend on occurrence of some other event or on passage of time, such as an interval between periodic sensing results operations. In other words, trigger detection is not necessary for other operations in FIG. 14 but could be beneficial; for example, a trigger detector can also provide size information about each object and can allow corresponding change in integration time or sensing pattern feature size, e.g. a larger bin size for larger particles.

The operation in box 802 then prepares for readout, such as by initializing data structures and obtaining values to be used during readout. As suggested in box 802, this operation could include a pre-sensing readout operation from which readout control parameters are obtained. Exemplary readout control parameters might include object position and speed, object size, fluid speed, sensing periods, and so forth, and some of these parameters could be measured using the same trigger detector that provided the trigger signal in box 800.

After the operation in box 802, appropriate subsequent operations can be performed for the type of sensing elements in the encoder/sensor, with a branch between alternative types of sensing elements represented by box 804; an actual implementation might be specialized for a specific type of sensing element, in which case the branch in box 804 and other branches described below would not need to be implemented as separate decision operations—only the operations for the specific type of sensing element would be required. Exemplary subsequent operations are illustrated for discrete photosensing elements, for discrete impedance-based sensing elements, and for CCD-type and CMOS-type photosensing arrays, but the techniques of FIG. 14 could also be implemented for other types of encoder/sensors, including types with more than one type of sensing elements or sensing elements of other types.

If the encoder/sensor includes discrete sensing elements that are photosensors or that are impedance-based sensing elements, appropriate subsequent operations can be performed, with a branch between photosensing and impedance-based sensing elements represented by box 810. As noted above, the branch in box 810 might not need to be implemented as a separate decision operation.

For impedance-based sensing elements such as electrodes, Hall effect sensor, inductors, etc., the operation in box 812 reads out and combines sensed values in an appropriate way. In the illustrated example, sensed values from impedance-based sensing elements are combined by being read out from leads through appropriate circuitry as an object has relative motion within the encoding/sensing region. Although the combined analog signal could be provided directly as sensing results, box 812 illustrates an implementation as in FIG. 13 in which sensed values are digitized or used in some other way to obtain motion-affected data. With appropriate circuitry, the use of common leads as in FIG. 13 can effectively add or multiply analog values from all the sensing elements in a sensing pattern, with the analog value from each sensing element at a given time indicating an object's effect on the sensing element at that time; therefore, if the object is sufficiently small relative to the minimum feature size of the arrangement's sensing pattern and if its relative motion within the encoding/sensing region does not exceed an appropriate maximum speed, the combined analog signal indicates a time-varying waveform for the object. Other circuitry could be used, for example, with implementations in which impedance-based sensors are read out in parallel.

For discrete photosensors, the operation in box 814 reads out sensed values in an appropriate way and the operation in box 816 combines them, also in an appropriate way, before they are provided in box 816. In the illustrated example, the operation in box 814 provides control signals that determine sensing periods for each photosensor, and, after each sensing period, can read out an analog value indicating a photosensed quantity during the sensing period. Various alternative readout techniques could be used with discrete photosensors having appropriate features; for example, if a photosensor has analog output that is continuously available and that, at any given time, indicates a photosensed quantity during a preceding interval, the analog output could be read out by sampling at appropriate intervals to obtain a series of analog values. To combine analog values read out in box 814 for a number of discrete photosensors, the operation in box 816 can illustratively digitize the analog values and then order the resulting digital photosensed quantities into a sequence in accordance with positions and extents of the photosensors and, if appropriate, an object's relative position and relative speed, resulting in a sequence of digital values that indicate one or more time-varying waveforms. The operation in box 816 can then provide this sequence of digital values as sensing results, such as for the object that had relative motion in the encoding/sensing region.

In ordering photosensed quantities into a sequence, the operation in box 814 performs a simple example of "time ordering", a term that refers herein to any operation that begins with a set of digital values or subsequences of digital values obtained from sensing results during a given period of time and that a resulting sequence of digital values that approximates an actual sequence of photosensed quantities or other sensed values that occurred in the period of time. Time ordering can therefore include, in addition to simple concatenation of digital values or subsequences, various operations in which digital values are smoothed, interpolated, combined at subsequence overlaps, or otherwise adjusted to produce the resulting sequence of digital values. The resulting sequence could exist in any appropriate form, e.g. as digital values stored in a sequence of actual or virtual memory locations, as a data structure in which digital values are in sequence, or as any other suitable type of sequence of digital values; where the raw sequence includes information that is redundant or unnecessary or that is unusable for some reason, the resulting sequence could be in a compressed form, e.g. with data indicating position in sequence and/or duration for each digital value or with any other suitable compression technique.

If the arrangement includes IC-implemented sensing elements that include photosensing cells in arrays on one or more ICs, different subsequent operations can be performed, with a branch depending on readout type being represented by box 820. As noted above, the branch in box 820 might not need to be implemented as a separate decision operation. Also, if arrays with other readout types are used, the subsequent operations could be implemented as appropriate for the particular readout types involved—CCD-type readout and CMOS-type readout are two exemplary approaches that are now commonly used, but other types might be developed in the future. Whatever type of readout is performed, an arrangement of IC-implemented sensing elements, such as with arrays of photosensing cells, can be used to flexibly approximate a number of different sensing patterns that could alternatively be implemented with discrete sensing elements.

The term "CCD" is an abbreviation for "charge-coupled device", which describes a type of circuitry that can operate as a photosensing cell in an array. Arrays of CCD devices, sometimes referred to herein as "CCD arrays", are typically read out with shifting techniques, sometimes referred to as "bucket brigade" techniques, in which photosensed quantities are shifted along a line of cells, whether a row or column; the term "CCD-type readout" therefore is used herein to encompass any readout technique in which photosensed quantities are shifted along a line of cells toward an end of the line at which they are received by readout circuitry. CCD-type readout could thus be implemented with an array of cells that are not CCDs, if the array includes appropriate circuitry so that it can be read out in this way, and all the lines of such an array could be shifted in parallel to read out the entire array.

To perform CCD-type readout, the operation in box 822 can shift lines of cells in an array to read out photosensed quantities from the array after each of a series of one or more appropriate sensing periods. The operation in box 824 can digitize photosensed quantities as they are shifted out of the array and can combine the photosensed quantities from groups of lines in accordance with one or more sensing patterns by "binning", which refers herein to an operation that obtains a combined value such as a value indicating a sum or product of the photosensed quantities shifted out of one or more lines of an array after one sensing period. For each pattern's binning in box 824, the operation in box 826 can then combine the binned quantities for the groups of lines by ordering them into an appropriate sequence to obtain a series of binned quantities that indicates one or more time-varying waveforms encoded in accordance with the pattern; for example, the binned quantities can be ordered into a sequence in accordance with positions and longitudinal widths of the groups in the pattern and, if appropriate, an object's position and speed relative to the encoding/sensing region, resulting in a sequence of digital values that indicate one or more time-varying waveforms encoded in accordance with the pattern. After the time-ordered combined sensing results for each pattern are obtained in box 826, the operation in box 828 can then provide them as sensing results.

The term "CMOS" is similarly an abbreviation for "complementary metal oxide semiconductor", which describes another type of circuitry that can operate as a photosensing cell in an array. In contrast to CCD-type readout, arrays of CMOS devices, sometimes referred to herein as "CMOS arrays", are typically read out in response to signals that can select any single line of cells of the array to be directly read out in parallel; in effect, a line of cells, such as a row, can be addressed and then read out. The term "CMOS-type readout" therefore is used herein to encompass any readout technique in which a single line of cells of the array can be selected and read out in parallel. CMOS-type readout could thus be implemented with an array of cells that are not CMOS devices, if the array includes appropriate circuitry so that it can be read out in this way; the entire array could be read out by selecting and reading out every line of the array in turn.

To perform CMOS-type readout, the operation in box 830 can select lines of cells in an array for readout in groups in accordance with one or more sensing patterns. For example, lines can be read out after each sensing period in a sequence in which the lines of each group in a pattern can be read out consecutively, one after another, so that they can be more easily combined than if lines of different groups were intermixed; as photosensed quantities for the lines of a group in a pattern are read out, the operation in box 832 can digitize and add them to obtain a sum of photosensed quantities for each group from a given sensing period. In an alternative approach, all the lines in the array can be read out and their photosensed quantities can be stored, after which the lines of groups in each pattern can be combined. As in box 826, the operation in box 834 can then combine the photosensed quantity sums for the groups of lines in each pattern by ordering them into an appropriate sequence to obtain a series of sums that indicates one or more time-varying waveforms encoded in accordance with the pattern; for example, the photosensed quantity sums can be ordered into a sequence in accordance with positions and longitudinal widths of the groups and, if appropriate, an object's position and speed relative to the encoding/sensing region, resulting in a sequence of digital values that indicate one or more time-varying waveforms encoded in accordance with the pattern. After the time-ordered combined sensing results for each pattern are obtained in box 834, the operation in box 836 can then provide them as sensing results.

Sensing results provided in boxes 828 and 836 can have substantially the same form as those provided in either of boxes 812 and 818. Appropriate scaling, shifting, normalization, and other suitable operations can be performed so that time-varying waveforms indicated by sensing results from different types of sensing elements have magnitudes and phases that allow comparison with each other or with reference waveforms.

If the encoder/sensor includes another type of sensing elements other than those handled as described above, an appropriate operation for the type of sensing elements can be performed, as shown in box 840. The operation in box 840 can read out and combine sensed values in any appropriate way to obtain sensing results, and the sensing results can then be provided in any appropriate way.

The operations in FIG. 14 are only exemplary, and various other combinations of operations could be performed to read out and combine sensed values from sensing elements of various types. Additional features of sensing results operations are described below in relation to specific implementations.

The operations in FIG. 14 are compatible with the techniques described above in relation to FIG. 7. If operating in control mode, for example, operations that provide control signals as in box 464 (FIG. 7) could be performed during readout as in one of boxes 812, 814, 822, 830, or 840 in FIG. 14. The operation in box 466 (FIG. 7) would also be performed by the readout operation in any of those boxes. In triggered sensing mode, on the other hand, the operation of obtaining data in box 472 (FIG. 7) could be implemented as explicitly indicated in box 812 in FIG. 14 or implicitly by digitizing, combining, and time-ordering combined sensing results as in box 816, boxes 824 and 826, or boxes 832 and 834.

Figure 15:
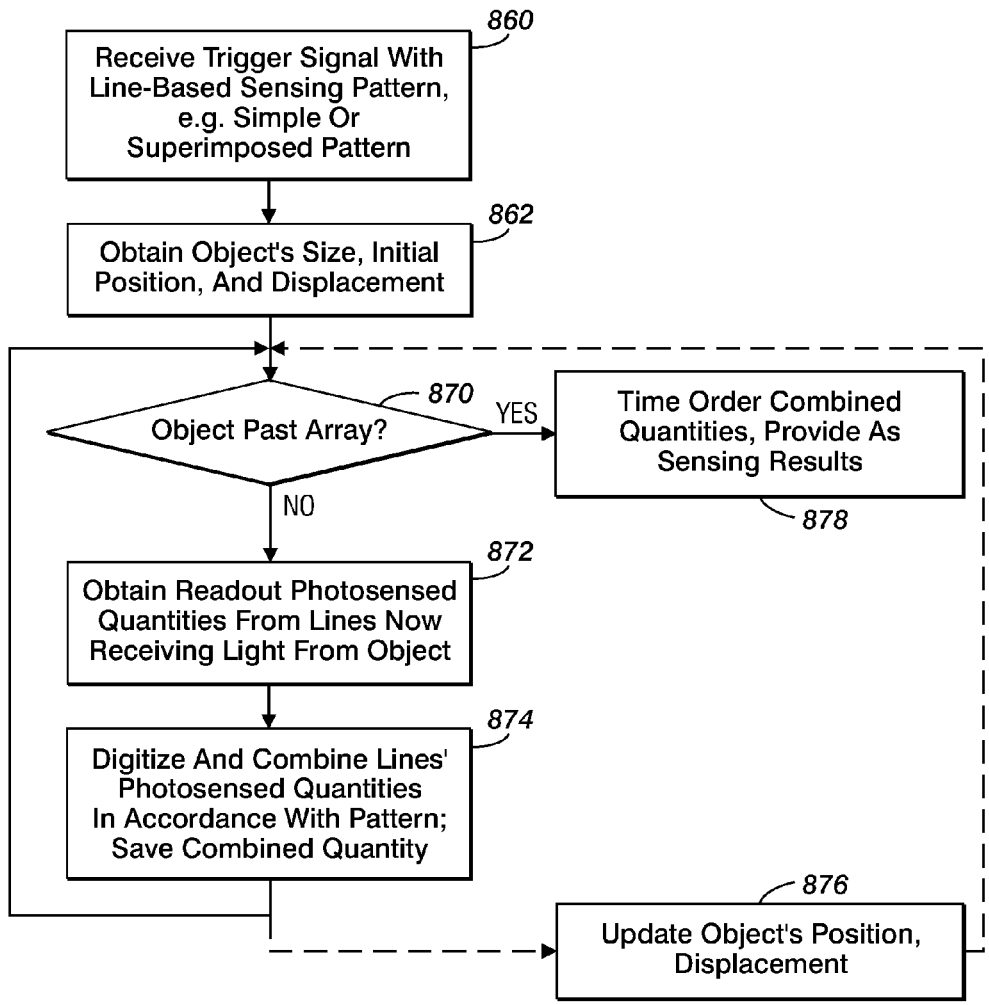
FIG. 15 is a flow chart showing features of a general technique that uses IC-implemented photosensing elements to obtain time-ordered sensing results, and that can implement some of the operations in FIG. 14.

FIG. 15 illustrates features of one general technique that uses IC-implemented monochromatic or multichromatic sensing elements to obtain time-ordered combined sensing results. The operations in FIG. 15 can be seen as an implementation of boxes 822 through 828 or of boxes 830 through 836 in FIG. 14.

The implementation of FIG. 15 begins with the operation in box 860 receiving a trigger signal that serves as a call to perform sensing results operations; the trigger signal can include, be accompanied by, or somehow explicitly or implicitly refer to a sensing pattern to be used during sensing results operations. As shown, however, the sensing pattern is "line-based", meaning that readout can be performed in accordance with the sensing pattern by reading out lines of an array of photosensing cells; in effect, the sensing pattern can be specified by specifying sensing characteristics for a sequence of lines, whether by specifying a repeating subsequence as in a periodic pattern, a single non-repeating sequence as in a non-periodic pattern, another type of sequence or subsequence, or even values for generating a sequence algorithmically or otherwise. In general, a line-based sensing pattern can be obtained that approximates another type of sensing pattern in which variation is predominantly in the longitudinal direction, e.g. a sensing pattern with parallel stripes, each having respective sensing characteristics and a respective width in the longitudinal direction; for complex patterns, all variations that are non-longitudinal could be ignored, and a respective digital value could be obtained for each position in the longitudinal direction, approximating the longitudinal variation to a desired level of resolution. The sensing pattern could be a "simple" pattern, in the sense that it is not a superposition of simpler patterns, such as a simple periodic or non-periodic pattern; the sensing pattern could also, however, be a superposition or scaled superposition of simpler patterns, e.g. if the simpler patterns are "parallel", meaning that the simpler patterns are all line-based patterns with lines sufficiently parallel that they can therefore be combined into a single line-based pattern, possibly after appropriate scaling of one or more patterns. When a line-based sensing pattern is obtained as a series of digital values, its relation to a particular array can also be specified by indicating the number of lines of the array that are included in each digital value of the pattern; this approach also makes it possible to use arrays with different but related cell sizes to implement a given sensing pattern at the same actual scale.

The operation in box 862 then prepares for readout, and can in general be implemented similarly to box 802 (FIG. 14). In particular, the operation in box 862 can obtain an object's size, initial position, and relative displacement, e.g., relative speed, and these values can later be used to identify lines of a photosensing array that are receiving emanating light from the object as it subsequently has relative motion within an encoding/sensing region from which light emanates to the array. The operation in box 862 can include appropriate signals to and from one or more of ICs 412 through 414 through IC I/O 410 (FIG. 6), and can also include appropriate signals to and from other devices through device I/O 420 (FIG. 6).

After the operation in box 862, the implementation of FIG. 15 performs a series of iterations, each of which begins with the operation in box 870, which determines whether the object's relative motion has gone out of the encoding/sensing region, such as based on the object's current position. Unless the object has left the encoding/sensing region, the next iteration is performed, obtaining combined quantities using photosensed quantities read out from lines receiving emanating light from the object. Assuming sufficient separation between objects, similar iterations could be concurrently but independently performed for more than one object, but the implementation of FIG. 15 relates to only one such object in an encoding/sensing region. In general, the operations in each iteration are similar to operations described above in relation to boxes 822, 824, 830, and 832 (FIG. 14), and could accordingly be implemented as appropriate for the readout type of the array, e.g. CCD-type readout, CMOS-type readout, or other, with appropriate signals to and from one or more of ICs 412 through 414 through IC I/O 410 (FIG. 6).

Each iteration begins with the operation in box 872, which obtains readout photosensed quantities from lines of photosensing cells that are receiving emanating light from the object at the time the iteration is performed; the term "readout photosensed quantities" is used herein to refer to photosensed quantities that have been read out. The operation in box 872 could be implemented in many different ways: At one extreme, all lines of the array could be read out as in box 822 (FIG. 14) and then only readout photosensed quantities could be selected that are from lines now receiving emanating light from the object; at another extreme, lines now receiving emanating light could first be identified and then only the identified lines could be consecutively selected and read out as in box 830 (FIG. 14); and other approaches could be intermediate between these extremes. In general, the operation in box 872 somehow identifies lines now receiving emanating light from the object, such as based on object size, position, displacement, and other information from box 862, possibly updated as described below. The operation in box 872 thus results in readout photosensed quantities from the identified lines being available for subsequent operations, which can be performed in real time or later, after read out is completed. In any case, readout photosensed quantities can be stored in memory 408 (FIG. 6) for further processing.

The operation in box 874 operates on readout photosensed quantities from box 872, digitizing and combining them in accordance with the sensing pattern from box 860, and then saving the resulting combined quantities in memory 408 (FIG. 6) or in another appropriate way so that they can be provided as sensing results, as described below. In the case of CCD-type readout, for example, readout photosensed quantities can be digitized as they are shifted out of the array and the digitized quantities for each line can be added to obtain a respective sum for the line; then, when the lines now receiving emanating light are identified, the respective sums of those lines can be similarly combined in accordance with the sensing pattern from box 860, such as by binning as in box 824 (FIG. 14) and/or performing other operations as appropriate. Similarly, in the case of CMOS-type readout, the lines now receiving emanating light can first be identified and then those lines can be read out consecutively in parallel into sample and hold circuitry (not shown), with each line's readout photosensed quantities then being similarly digitized and added to obtain a respective sum for the line; then, the sums can be combined in accordance with the sensing pattern from box 860, such as by adding as in box 832 (FIG. 14) and/or performing other operations as appropriate.

The operation in box 874 can take into account various features of the sensing pattern from box 860. For example, when emanating light is being received on both sides of a boundary between stripes within the sensing pattern, photosensing results could simply be discarded; in a more complex implementation, lines on each side of the boundary could be separately binned or added and saved for subsequent operations. Where a sensing pattern is intensity-dependent, photosensed quantities could be scaled in accordance with the specified intensity of each stripe of the pattern at any appropriate time, such as by analog operations immediately when read out or by digital operations after being digitized, after being combined for a line, or after being combined for a group of lines within the stripe. Similarly, where a sensing pattern is spectrum-dependent and readout photosensed quantities include spectral information such as by being in an RGB pattern, readout photosensed quantities could be selected for binning or adding in accordance with the specified spectrum of each stripe of the pattern.

After the operation in box 874, the operation in box 876 can be optionally performed as indicated by the dashed lines to and from box 876. This operation updates information about the object's position and displacement, making it possible to more accurately identify lines that are receiving emanating light from the object in the next iteration. This operation could be performed in every iteration or it might never be performed; also, each iteration could include a decision whether to perform this operation based, e.g., on photosensed quantities read out and combined in boxes 872 and 874 or on other information obtained in the current iteration.

When the operation in box 870 determines that the object is past the array, i.e. has left the encoding/sensing region, the operation in box 878 time orders the combined quantities from iterations of box 874 and provides the resulting time-ordered combined quantities as sensing results that indicate one or more time-varying waveforms, such as to external circuitry through external I/O 406 or by storing the sensing results in appropriate data structures in memory 408 or in one of devices 422 through 424 by appropriate signals to device I/O 420 (FIG. 6). The time ordering operation in box 878 can include various appropriate adjustments to obtain improved sensing results. For example, where emanating light from an object is approximately constant across each stripe of a sensing pattern, the combined quantities from iterations of box 874 that include values from that stripe can be used to obtain a single value that is provided for each frame of that stripe, where the term "frame" is used herein to refer to a unit of time for which one value or one set of concurrent values is provided in the time-ordered combined quantities; if the iterations occur with a constant period, each frame could have the same proportionality relationship to the length of each iteration, with, e.g., j iterations per frame or with k frames per iteration. More generally, the time-ordered combined quantities that form the sensing results can be time scaled or otherwise adjusted in any appropriate way so that they accurately reflect light emanating from the object as a function of time.

If the sensing pattern from box 860 is purely binary, it can be treated, in effect, as two complementary patterns that can both be applied in operations in box 874; in other words, line groups that are on in the sensing pattern would be binned together in a first binning operation, while line groups that are off would be omitted, while line groups that are off in the sensing pattern would be binned together in a second binning operation, while line groups that are on would be omitted, with the result that all photosensed quantities are binned in one of the two operations. As a result, the operation in box 878 can produce two complementary sequences of values, one for each of the complementary patterns, and appropriate further operations can be performed to combine the complementary sequences into a single combined sequence of values, such as to improve signal-to-noise ratio due to redundant information in the complementary sequences. This technique may be especially useful with rapid CCD-type readout in which all lines are being read out in any case, so that the only additional operations are the digitization and binning after each shifting operation; high quality CCD-type readout devices are currently available with peak quantum efficiency exceeding 90% and with sampling rates as fast as 30 MHz.

Some techniques as in FIG. 15 can be implemented without filters or masks, because binning or other appropriate operations on photosensed quantities from selected lines takes the place of masking. More flexible techniques could be implemented by saving each line's respective combined quantity in box 874, and then further combining those quantities in accordance with any appropriate number of sensing patterns in box 878 prior to time ordering; in a particularly useful example, the respective quantities of lines could first be binned or otherwise selected and/or combined in accordance both with a periodic pattern (e.g. every nth line) and a random, chirp, or other non-periodic pattern—the periodic sensing results could be used to obtain speed or other displacement information about an object, and the non-periodic sensing results could be used, together with time-scaled comparison based on the displacement information, to obtain information about the object's position or type, such as with techniques as described in co-pending U.S. patent application Ser. No. 12/022,485, entitled "Obtaining Information from Time Variation of Sensing Results" and incorporated herein by reference in its entirety. Also, since it is not necessary to optimize, make, and align a mask for a specific cell diameter or other object size or characteristic, it is possible to combine the respective combined quantities of groups of lines as appropriate for different object sizes or other characteristics after the lines' combined quantities have been obtained and saved; in effect, a pre-analysis operation could be performed on the lines' combined quantities to extract information about an object, e.g. by binning in accordance with a chirp pattern or a random pattern with small feature size or even with a staircase periodic pattern. After pre-analysis, a technique according to these variations could branch based on the extracted information, such as by binning the combined quantities as appropriate for the object size obtained in pre-analysis. It might be possible to implemented variations of the technique in FIG. 15 to efficiently replace techniques previously used for detecting object size and position, such as Mie scattering and so forth.

Figure 16:
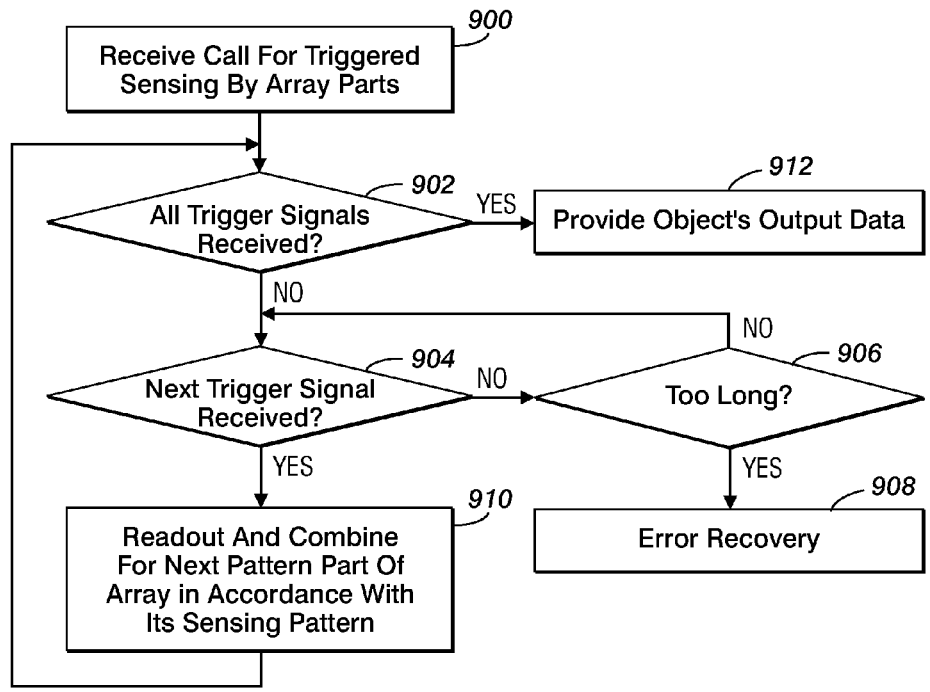
FIG. 16 is a flow chart showing readout operations that can be performed in an implementation as in FIG. 5 with a photosensing array and control circuitry that includes a processor.

The flow chart in FIG. 16 illustrates how triggered encoding/sensing techniques similar to those described above could be implemented with a photosensing IC without separate trigger detector circuitry, such as with CPU 402 (FIG. 6) operating as control circuitry. In other words, an array of photosensing cells on the IC includes parts that operate as trigger detectors and other parts that operate as encoder/sensors.

The technique of FIG. 16 illustratively reads out some parts of an array, i.e. "trigger parts", to obtain trigger signals that can be used to control readout operations for respective other parts of the same array, i.e. "pattern parts"; the pattern parts can implement respective sensing patterns. The technique of FIG. 16 could be implemented, for example, in an additional triggered sensing routine that could be executed by CPU 402, in the course of which appropriate calls to routine 442 could be made to perform sensing results operations. Although suitable for CPU 402, operations in FIG. 16 could be implemented with a wide variety of different types of circuitry with or without a CPU, possibly including circuitry integrated on the same IC with an array that includes the trigger parts and the pattern parts.

In the operation in box 900, CPU 402 receives a call for triggered sensing by array parts. In flexible implementations, the call could specify or otherwise indicate which parts of the array are to serve as trigger parts and which parts are to serve as pattern parts; the call could similarly specify, for each pattern part, the respective sensing pattern, such as a periodic pattern with a given period or a random, chirp, or other appropriately specified non-periodic pattern. In response, the operation in box 900 can perform appropriate initialization and other preliminary operations, such as to set appropriate values indicating the first trigger and pattern parts on the array.

The operation in box 902 then begins an outer iterative loop that can continue until all trigger parts provide photosensed quantities indicating that the object has entered their respective trigger detection regions. Each outer iterative loop includes one or more iterations of an inner iterative loop, which begins with the operation in box 904 testing the next trigger part along the array to determine whether its photosensed quantities indicate detection of the object in its trigger detection region. If not, the operation in box 906 can use an appropriate time limit or other criterion to determine whether it has been too long for the object to be detected by the next trigger part, in which case the operation in box 908 can initiate appropriate error recovery operations (not shown). If it has not been too long, the operation in box 904 is again performed.

When the operation in box 904 determines that the next trigger part's photosensed quantities indicate detection of the object, the outer iterative loop continues to the operation in box 910. In box 910, CPU 402 can provide appropriate calls, e.g., to sensing results routine 442 (FIG. 6), so that photosensed quantities from the next pattern part of the array are appropriately read out in accordance with its sensing pattern. The operation in box 910 might be implemented to use information from previous pattern parts of the same array to determine parameters of the sensing pattern, such as its time scale.

Finally, when all the trigger parts have provided appropriate trigger signals and all the pattern parts have been read out, the operation in box 912 provides the object's output data in any appropriate form. The output data could include characteristic data about the object's characteristics, type data about the object's type, sensing results data indicating one or more time-varying waveforms, or other data obtained from sensing results from the pattern parts.

The technique of FIG. 16 is similar to a trigger and gate mechanism that records portions of an object's emanation intensity that exceed a threshold magnitude, then applies a window function to this finite signal. A trigger and gate mechanism could be used where objects are sufficiently spaced that each object's time-varying signal can be isolated from those of preceding and following objects. After application of the window function, appropriate other operations could be performed, such as a Fourier transform to obtain a scaling factor for use in time-scaled comparison.

In general, fluidic techniques as described above involve a sufficiently diluted sample or employ conventional flow cytometry techniques so that only one distinguishable object at a time is likely to be in a trigger detector region and then in its downstream encoding/sensing region. If two or more objects travel together past a trigger detector or a trigger part of an array, a triggering technique as described above might blindly produce overlapping sensing results for the objects as if they were one object. To resolve this problem, a Fourier transform of sensing results can be analyzed to find subpeaks that have a high probability of resulting from periodic signals from multiple objects traveling at different speeds. Each subpeak's scaling factor can be obtained for use in time-scaled comparison, and correlation or other comparison can be performed with each scaling factor to obtain correlation results for each object. Even if an error is made, such as by identifying a spurious subpeak, the correlation results can be analyzed to determine whether a signal emanating from an object moving at the counterpart speed was sensed.

Figure 17:
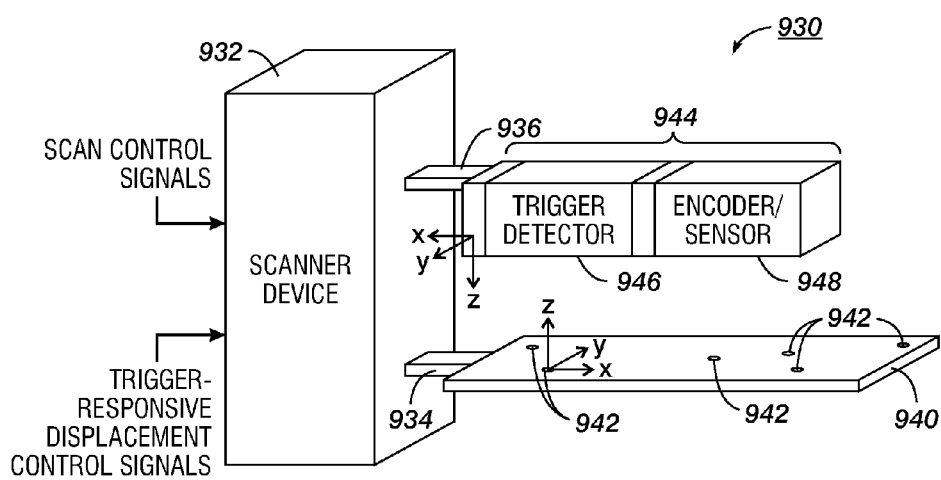
FIG. 17 is a partially schematic perspective view of a system that can be implemented as in FIG. 6 and that includes a scanner device.
Figure 18:
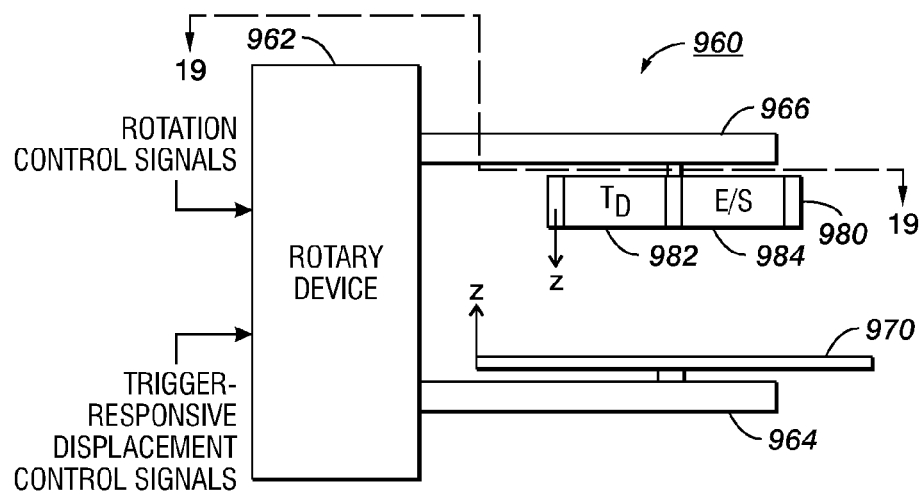
FIG. 18 is a partially schematic side view of a system that can be implemented as in FIG. 6 and that includes a rotary device.
Figure 19:
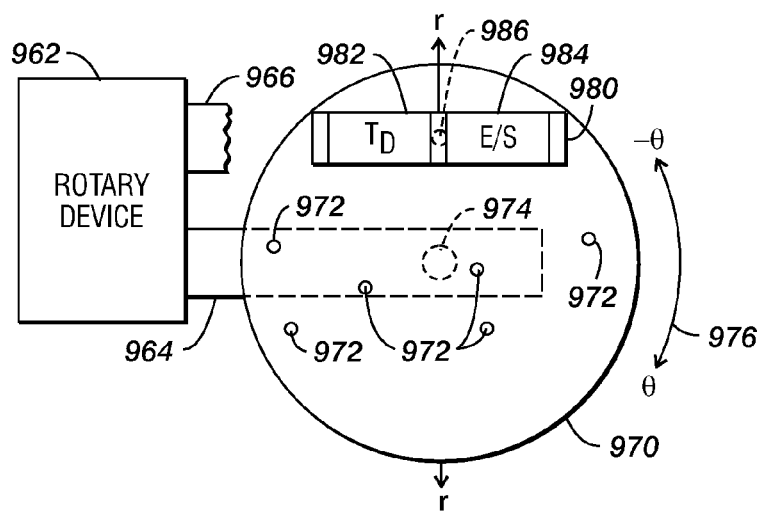
FIG. 19 is a partially schematic cross-sectional top view, taken along the line 19-19 in FIG. 18.

As indicated above, many exemplary techniques described herein are not limited to implementations in which relative motion in fluidic structures is caused by fluidic devices, but could be used with other types of relative motion, including relative motion caused by non-fluidic devices and in non-fluidic structures. FIGS. 17-19 illustrate examples in which non-fluidic devices produce relative motion in ways that could be used in combination with the techniques such as those in FIGS. 14-16. In general, the techniques in FIGS. 17-19 can be implemented in various ways, including, in some cases, certain features shown and described in U.S. Pat. No. 7,420,677, incorporated herein by reference in its entirety.

The implementations illustrated in FIGS. 17-19 allow relative motion between two components, one of which includes a support structure on which one or more objects are supported and the other of which includes an object interaction unit with a trigger detector and an encoder/sensor. In the illustrated examples, both of these components can be moved by a device in response to control signals, but the techniques described could be implemented with systems in which one of the components is stationary and only the other one is moved by the device in response to control signals. Furthermore, the illustrated implementations could be operated in this manner simply by holding one component stationary, although this would reduce the possible range of relative motion in some cases.

In the implementations in FIGS. 17-19, the support structure could take any suitable form, such as a slide on which objects are positioned, a disk on which objects are positioned, or even a fluidic device within which objects are immobilized, such as by binding to particles within a gel, or are moving slowly relative to the nonuniform relative motion caused by device operations; the support structure could also include, for example, a pair of slides with objects positioned between them such as in sputum or other liquid, a capillary tube containing objects, a biochip, an array of wells, a well plate, and so forth, any of which could be positioned on another part of the support structure such as a scanner bed or rotating disk. The object interaction units could similarly be implemented in a wide variety of ways with various types of trigger detectors and encoder/sensors positioned relative to each other in various ways; the detection and sensing could make use of any suitable type of interaction, including optical sensing of light emanating from objects, impedance-based sensing such as with electrodes or Hall effect devices, or even possibly piezoelectric or other pressure-based sensing of acoustic signals emanating from objects. Furthermore, the encoder/sensor can include any suitable combination of circuitry, including circuitry to control, for example, excitation, filtering, and sensing; in optical implementations, an object interaction unit could include an IC with an array of photosensing cells, operated as described above with one or more trigger parts that serve as trigger detectors and one or more pattern parts that serve as encoder/sensors.

System 930 in FIG. 17 includes scanner device 932 with support components 934 and 936. Support structure 940 is mounted on support component 934, and it supports a number of distinguishable objects 942. Object interaction unit 944 is mounted on support component 936, and it includes at least one trigger detector 946 and at least one encoder/sensor 948. As illustrated by the two complementary sets of x-, y-, and z-axes for one of objects 942 and for object interaction unit 944, any specified relative motion between support structure 940 and object interaction unit 944 can be accomplished by moving either or both of them such that the net result of their movements is the specified relative motion. The x-axis indicates a scanning direction in which scanner device 932 can cause relative motion between object interaction unit 944 and support structure 940 such that a given object 942 can have relative motion into a trigger detection region relative to trigger detector 946, then from the trigger detection region into an encoding/sensing region relative to encoder/sensor 948, and then within the encoding/sensing region, resulting in motion-affected sensing results or data as described above. The y-axis illustrates a direction of relative motion in which the distance between support structure 940 and object interaction unit 944 can remain constant, but displacement can occur perpendicular to the scanning direction. The z-axis illustrates a direction in which support structure 940 and object interaction unit 944 can move closer to or farther away from each other.

In operation, scanner device 932 responds to scan control signals, such as from CPU 402 through device control IO 420 (FIG. 6), by moving support structure 940 and/or object interaction unit 944 to produce relative motion in the scanning direction; CPU 402 could, for example, provide the scan control signals while executing operating routine 440 (FIG. 6). Then, when trigger detector 946 provides a trigger signal indicating relative motion of one of objects 942 into its trigger detection region, CPU 402 can execute sensing results routine 442 and provide trigger-responsive displacement control signals to scanner device 932, which responds with movement of one or both of support structure 940 and object control unit 944 to produce displacement while object 942 has relative motion within the encoding/sensing region of encoder/sensor 948. Displacement in any of the three directions indicated by the x-, y-, z-axes can be used to obtain motion-affected sensing results and/or data that indicate time-varying waveforms with information resulting from the relative motion to which support structures 970 and 980 are stably attached; for added precision, it might also be possible to independently displace trigger detector 982 and encoder/sensor 984, such as in the z-direction. In particular, displacement in any of the three indicated directions can include one or more modulation cycles within the encoding/sensing region, so that the scanning motion is a carrier component and the displacement includes modulation cycles.

FIGS. 18 and 19 show system 960 from a side view and from a top view with partial cross section, respectively. System 960 includes rotary device 962, a device that can produce rotating motion through one or both of support components 964 and 966; rotary device 962 might, for example, be a miniaturized device such as a MEMS or nanotechnology device. Support structure 970 is illustratively circular, supporting objects 972, but could have any appropriate shape and in other respects could be implemented similarly to support structure 940 in FIG. 17. Support structure 970, however, can rotate about axis 974 as indicated by bidirectional arrow 976. Object interaction unit 980, similarly to object interaction unit 944 in FIG. 17, includes trigger detector (TD) 982 and encoder/sensor (E/S) 984. Object interaction unit 980 can also illustratively rotate about axis 986, although that type of relative motion is not employed in the particular technique illustrated in FIGS. 18 and 19. Various additional types of motion are possible, such as independent height adjustment in the z-direction for TD 982 and E/S 984.

Three dimensions of relative motion illustrated in FIGS. 18 and 19 include a θ-direction that is a direction of rotation indicated by arrow 976 and that can be measured as an angle of rotation; an r-direction that can be measured as a distance from an axis of rotation of support structure 970 to object interaction unit 980; and a z-direction that is the same as the z-direction in FIG. 17. For example, while support structure 970 is rotating in the θ-direction, an object 972 can have relative motion into the trigger detection region of trigger detector 982, with the rotating motion being produced by rotary device 962 in response to rotation control signals, similar to the scan control signals described above in relation to FIG. 17. Then, in response to trigger-responsive displacement control signals from CPU 402 (FIG. 6) as described above, rotary device 962 can produce displacement in any of the θ, r-, and z-directions while object 972 has relative motion within the encoding/sensing region of encoder/sensor 984. As indicated by the complementary r-axes and z-axes on support structure 970 and on object interaction unit 980, rotary device 962 can produce displacement in these two directions by moving one or both of support components 964 and 966 to which support structures 970 and 980 are stably attached; for added precision, it might also be possible to independently displace trigger detector 982 and encoder/sensor 984, such as in the z-direction. As above, the resulting displacement can provide motion-affected sensing results and/or data. In particular, the displacement can include one or more modulation cycles within the encoding/sensing region, so that the rotating motion is a carrier component and the displacement includes modulation cycles.

In the above-described implementations of scanning device 932 and rotary device 962, information is encoded as result of relative motion within encoding/sensing regions in response to trigger signals, and the relative motion illustratively controls displacement caused by trigger-responsive control signals. Encoding could instead, however, be performed without trigger-responsive displacement, such as by providing control signals to one or more of excitation, filter, or sensing circuitry within encoder/sensors 948 and 984. Furthermore, various other modifications could be made in the above-described techniques to obtain motion-affected sensing results and/or data.

Implementations as described above in relation to FIGS. 1-19 could be advantageously applied in a wide variety of sensing applications, possibly including, for example, fluorescence- or impedance-based flow cytometry or other biodetector applications that seek a signature of a particle of unknown velocity; such biodetectors often use microfluidic channels with inhomogeneous flow profiles, causing variation in particle velocity. The techniques can be used to count or obtain ratios between fluorescing objects of different types, such as different types of tagged cells, particles, tagged DNA, and so forth. In such an application, calibration can be performed using known objects, e.g. tagged beads, with known velocities to obtain template waveforms that include deviations caused by fabrication tolerances but can then be compared with sensed waveforms to obtain information about unknown objects.

Implementations described above may be advantageous in biodetector applications that require compact, low-cost components without critical optics and with high sensing efficiency. Such applications might include point-of-care flow cytometry (such as with an integrated flow cytometer), DNA analysis, proteomics, and so forth.

Also, implementations described above could be applied in scanning of bio-chips or documents where objects have different emanation spectra, and so forth. The techniques may also be applicable in various low S/N ratio systems in which a known signal is bounced off an object traveling at an unknown velocity, such as where object velocity is on the order of signal propagation velocity, as in SONAR. The techniques may be especially advantageous where precise information about position, speed, or type of objects is sought.

Some of the implementations described in relation to FIGS. 1-19 are examples of apparatus that includes an encoder/sensor, a trigger detector, a relative motion component, and a circuitry component. The encoder/sensor obtains sensing results from objects in an encoding/sensing region relative to the encoder/sensor. The trigger detector responds to each of a set of distinguishable objects; when the object is in a trigger detection region relative to the trigger detector, the trigger detector provides a respective trigger signal. The relative motion component causes relative motion of a subset of the distinguishable objects into the trigger detection region, from the detection region into the encoding/sensing region, and within the encoding/sensing region. The circuitry component includes control circuitry and/or processing circuitry. The control circuitry, in response to an object's trigger signal, provides control signals that cause one or both of the encoder/sensor and the relative motion component to operate so that the encoder/sensor obtains respective encoded sensing results indicating at least one time-varying waveform with information resulting from the object's relative motion within the encoding/sensing region. The processing circuitry, in response to an object's trigger signal, obtains data from the sensing results, and the data indicate at least one time-varying waveform with information resulting from the object's relative motion within the encoding/sensing region.

In specific implementations, the apparatus can include a fluidic structure with a channel that includes the trigger detection region and, downstream from the trigger detection region, the encoding/sensing region; the relative motion component can cause relative motion of objects through the channel. At least some of the control signals from the control circuitry can be provided to the relative motion component, which can include a fluid motion mechanism, a channel motion mechanism, a support motion mechanism, and/or an encoder/sensor motion mechanism, each of which can, in response to control signals, change timing, relative speed, and/or relative direction of objects' relative motion within the encoding/sensing region. The fluid motion mechanism can do so by controlling flow of fluid carrying the objects; the channel motion mechanism by controlling movement of a channel through which the objects are carried by fluid; the support motion mechanism by controlling movement of a structure supporting the objects; and the encoder/sensor motion mechanism by controlling movement of the encoder/sensor.

In further specific implementations, the relative motion component can include both the fluidic motion mechanism and the channel motion mechanism described above, with the fluidic motion mechanism controlling flow of fluid approximately parallel to a flow direction in the channel and the channel motion mechanism controlling movement of the channel in a transverse direction approximately perpendicular to the flow direction. Or the apparatus can include a movable part that can hold the structure supporting the objects, and the support motion mechanism can include a scanner device and/or a rotary device, each of which responds to the control signals. Or, the apparatus can include a movable part that holds the encoder/sensor, and the encoder/sensor motion mechanism can include a scanner device and/or a rotary device, either of which responds to control signals. In both of the latter cases, the scanner device can control scanning movement of the movable part in at least one scanning direction, and the rotary device can control rotating movement of the movable part.

In further specific implementations, the encoder/sensor can include excitation circuitry, displacement circuitry, filter circuitry and/or sensor circuitry, and at least some of the control signals are provided to the encoder/sensor. The excitation circuitry can provide time-varying excitation to objects in the encoding/sensing region, and each of the objects in the subset emanates light in response to the time-varying excitation as the object has relative motion within the encoding/sensing region. The displacement circuitry can provide time-varying displacement of objects in the encoding/sensing region, and each of the objects in the subset is displaced relative to the channel as the object has relative motion within the encoding/sensing region. The filter circuitry can provide time-varying filtering of light emanating from objects in the encoding/sensing region, providing the time-varying filtering of light from each of the objects in the subset as the object has relative motion within the encoding/sensing region. The sensor circuitry can include a longitudinal sequence of two or more photosensing elements along the encoding/sensing region and can read out and combine photosensed quantities from a subsequence of two or more of the photosensing elements to provide combined encoded sensing results for each of the objects in the subset as it has relative motion within the encoding/sensing region and emanates light; the combined encoded sensing results indicate a time-varying waveform resulting from the object's relative motion within the encoding/sensing region.

In further specific implementations that include the filter circuitry, the filter circuitry can include liquid crystal display (LCD) circuitry that causes operation of an LCD filter as each of the objects has relative motion within the encoding/sensing region. In specific implementations that include the sensor circuitry, the longitudinal sequence can include two or more discrete photosensors and/or two or more photosensing cells in a photosensing array on an integrated circuit (IC). In specific implementations with photosensing cells, the trigger detector can include a first set of cells in the photosensing array and the sensor circuitry can include a second set of cells, with the trigger detection region being along the first set of cells and the encoding/sensing region being along the second; in addition, the circuitry component can include the processing circuitry, which can provide readout control signals to the IC and, in response, receive readout quantity signals from the IC that indicate photosensed quantities from cells of the array.

In further specific implementations with processing circuitry, the encoder/sensor can include a photosensor and/or an impedance-based sensor. The processing circuitry can be programmed to respond to an object's trigger signal by providing readout control signals to the photosensor to obtain readout photosensed quantities. Or the processor can be programmed to respond to an object's trigger signal by obtaining readout impedance-based quantities from the impedance-based sensor. In further specific implementations, the trigger detector can include one or more photosensors, one or more cells of a photosensing array, a Coulter counter, and/or a Mie scatter sensor.

In further specific implementations in which the circuitry component includes control circuitry, the control circuitry can include a processor programmed to provide the control signals in response to the object's trigger signal. The circuitry component can also include the processing circuitry, which can include the processor, also programmed to obtain the data from the sensing results in response to the object's trigger signal. The control circuitry can provide control signals only to the encoder/sensor in response to the object's trigger signal, and the relative motion component can operate independently of the object's trigger signal; alternatively, the control circuitry can provide control signals both to the encoder/sensor and to the relative motion component.

Some of the implementations described in relation to FIGS. 1-19 are examples of apparatus that includes an array of photosensing cells on an IC, a relative motion component, and a circuitry component. The array includes first and second sets of photosensing cells, with the first set photosensing light emanating from each of a set of distinguishable objects when the object is in a detection region relative to the first set, and with the second set photosensing light emanating from objects in an encoding/sensing region relative to the second set. The relative motion component causes relative motion of a subset of the distinguishable objects into the detection region, from the detection region into the encoding/sensing region, and within the encoding/sensing region. The circuitry component reads out photosensed quantities from the first and second sets of photosensing cells and, in response to photosensed quantities from the first set indicating light emanating from one of the subset of objects in the detection region, obtains data from photosensed quantities from the second set; the data indicate at least one time-varying waveform with information resulting from the object's relative motion within the encoding/sensing region.

Some of the implementations described in relation to FIGS. 1-19 are examples of a method of using trigger detectors and encoder/sensors. The method causes relative motion of a distinguishable object into a trigger detection region, from the trigger detection region into an encoding/sensing region, and within the encoding/sensing region. During the relative motion, the method operates a trigger detector to provide a trigger signal when the object is in the trigger detection region, which is relative to the trigger detector; the method also operates an encoder/sensor to obtain sensing results when the object is in the encoding/sensing region, which is relative to the encoder/sensor. During the relative motion, the method also responds to the trigger signal in at least one of the following ways: The method controls at least one of the encoder/sensor's operation and the object's relative motion within the encoding/sensing region so that the encoder/sensor obtains encoding sensing results indicating at least one time-varying waveform with information resulting from the object's relative motion within the encoding/sensing region and/or the method obtains data from the sensing results, with the data indicating at least one such time-varying waveform.

In specific implementations, the method can provide time-varying excitation in the encoding/sensing region, time-varying displacement of the object, and/or time-varying filtering of light emanating from the encoding/sensing region. The method can also obtain photosensed quantities from a longitudinal sequence of photosensing elements as described above and combine the photosensed quantities to obtain combined encoded photosensing results.

In further specific implementations, the trigger detector can include a trigger part of a photosensing cell array on an IC, and the encoder/sensor can include a sequence part of the array with photosensing cells in a longitudinal sequence. The method can operate the trigger detector by causing readout of photosensed quantities from the trigger part and can, in response to readout photosensed quantities from the trigger part indicating detection of the objects, cause readout of the sequence part.

In further specific implementations, the encoder/sensor can include an arrangement of discrete photosensors. In controlling the encoder/sensor's operation, the method can cause readout of the discrete photosensors.

In further specific implementations in which the method provides displacement of the object's relative motion within the encoding/sensing region, the method can control flow of fluid carrying the object, control movement of a channel through which the object is carried by fluid, control movement of a structure supporting the object, and/or control movement of the encoder/sensor.

Some of the implementations described in relation to FIGS. 1-19 are examples of apparatus that includes a fluidic structure, a trigger detector, and an encoder/sensor. The fluidic structure includes a channel within which objects can have relative motion in a longitudinal direction during operation. The trigger detector is along the channel upstream from an encoding/sensing region and responds to each of a set of distinguishable objects as the object has relative motion into a trigger detection region relative to the trigger detector; the trigger detector responds by providing a respective trigger signal. The encoder/sensor responds to an object's trigger signal, obtaining respective sensing results while the object has relative motion within the encoding/sensing region, and the sensing results indicate at least one time-varying waveform with information resulting from the relative motion. The encoder/sensor includes excitation circuitry, displacement circuitry, filter circuitry, and/or sensor circuitry, each of which is as described above.

In specific implementations, the apparatus can be a flow cytometer. The apparatus can also include control circuitry that receives the trigger signals and, in response, provides control signals that cause the encoder/sensor to obtain the object's sensing results; the control circuitry can include a processor. In general, the apparatus can include other features mentioned above.

Exemplary implementations described above employ photosensors or impedance-based sensors with specific features, but a wide variety of sensors could be used to obtain sensing results indicating values of various parameters other than emanating light intensity, parameters that can have time variation that indicates information resulting from relative motion of objects within encoding/sensing regions. Similarly, implementations described above involve sensing information resulting from relative motion of objects in fluidic channels or relative to a sensor such as in scanning or rotation, but various other types of fluidic implementations or other implementations in which objects have relative motion in various other ways could be sensed to obtain sensing results as in techniques described above.

Components of exemplary implementations as described above could have various shapes, dimensions, or other numerical or qualitative characteristics other than those illustrated and described above. Similarly, although the exemplary fluidic implementations generally involve sensing from a single fluidic channel, implementations could readily include multiple parallel channels, allowing parallel sensing and readout and larger scale sensing.

Some of the above exemplary implementations involve specific types of trigger detectors, encoder/sensors, relative motion components, control circuitry, processing circuitry, and so forth, but the invention could be implemented with a wide variety of other types of components. For example, some implementations use specific types of spatial modulation based on one or more of an excitation pattern, a filter assembly, a sensing pattern, and/or displacement control, but various other types of spatial modulation could be used, including any appropriate combination of color, gray scale, and black and white patterning and including other patterning techniques; for example, in a fluidic implementation, a patterned photosensor could be printed or otherwise produced on an inward wall or other boundary of a channel or in another appropriate location. Also, some exemplary implementations use specific types of processing, such as digital signals obtained after converting sensed analog values. In general, however, the invention could be implemented with any suitable signal processing techniques, including any appropriate combination of analog and digital processing; photosensed quantities could be combined either in analog or digital form; either or both of two compared waveforms could be obtained in analog or digital form, and any combination of time scaling could be performed before comparison. Further, some exemplary implementations use discrete, large area photosensors or impedance-based sensors, but various ICs with photosensing arrays might be used.

Some of the above exemplary implementations involve specific types of emanating light, e.g. fluorescence, and specific types of excitation, filtering, and photosensing suitable to fluorescent light, but these are merely exemplary. The invention could be implemented in relation to various other types of emanating light with various other types of excitation, filtering, and photosensing in various other ranges of photon energies or with any other appropriate sensed stimuli.

Some of the above exemplary implementations involve specific materials, such as in fluidic structures with light-transmissive components or in filtering arrangements with reflective material or light blocking material such as amorphous silicon, but the invention could be implemented with a wide variety of materials and with layered structures with various combinations of sublayers. Thicknesses of layers may vary across any suitable range.

The exemplary implementation in FIG. 6 employs a CPU, which could be a microprocessor or any other appropriate component. Furthermore, as noted above, operations could be performed digitally or with analog signals, and could be done either on the same IC as a photosensor array, on other components, or on a combination of the two, with any appropriate combination of software or hardware.

The above exemplary implementations generally involve use of trigger detectors, encoder/sensors, relative motion components, control circuitry, processing circuitry, and so forth following particular operations, but different operations could be performed, the order of the operations could be modified, and additional operations could be added within the scope of the invention. For example, readout of sensed quantities from a sensor to obtain a sensed time-varying waveform could be performed serially or in parallel, and, with an array, could be performed cell-by-cell, line-by-line, or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. Apparatus comprising:
   an encoder/sensor that obtains sensing results from objects in an encoding/sensing region relative to the encoder/sensor;
   a trigger detector that responds to each of a set of distinguishable objects when the object is in a trigger detection region relative to the trigger detector, providing a respective trigger signal;
   a relative motion component that causes relative motion of a subset of the distinguishable objects into the trigger detection region, from the trigger detection region into the encoding/sensing region, and within the encoding/sensing region; and
   a circuitry component that includes at least one of: control circuitry that, in response to the respective trigger signal of an object in the subset, provides control signals that cause one or both of the encoder/sensor and the relative motion component to operate so that the encoder/sensor obtains respective encoded sensing results indicating at least one time-varying waveform with information resulting from the object's relative motion within the encoding/sensing region; and
   processing circuitry that, in response to the respective trigger signal of an object in the subset, obtains data from the sensing results, the data indicating at least one time-varying waveform with information resulting from the object's relative motion within the encoding/sensing region.

2. The apparatus of claim 1, further comprising:
   a fluidic structure with a channel that includes the trigger detection region and the encoding/sensing region, downstream from the trigger detection region; the relative motion component causing relative motion of objects through the channel.

3. The apparatus of claim 1 in which the circuitry component includes the control circuitry and at least some of the control signals are provided to the encoder/sensor; the encoder/sensor comprising at least one of:
   excitation circuitry that, in operation, provides time-varying excitation to objects in the encoding/sensing region; each of the objects in the subset emanating light in response to the time-varying excitation as the object has relative motion within the encoding/sensing region;
   displacement circuitry that, in operation, provides time-varying displacement of objects in the encoding/sensing region; each of the objects in the subset being displaced relative to the channel as the object has relative motion within the encoding/sensing region;
   filter circuitry that, in operation, provides time-varying filtering of light emanating from objects in the encoding/sensing region; the filter circuitry providing time-varying filtering of light emanating from each of the objects in the subset as the object has relative motion within the encoding/sensing region; and
   sensor circuitry that includes a longitudinal sequence of two or more photosensing elements along the encoding/sensing region and that, in operation, reads out and combines photosensed quantities from a subsequence of two or more of the photosensing elements to provide combined encoded sensing results for each of the objects in the subset as the object has relative motion within the encoding/sensing region and emanates light, the combined encoded sensing results indicating a time-varying waveform resulting from the object's relative motion within the encoding/sensing region.

4. The apparatus of claim 3 in which the encoding/sensing circuitry includes the filter circuitry; the filter circuitry including liquid crystal display (LCD) circuitry that causes operation of an LCD filter as each of the objects in the subset has relative motion within the encoding/sensing region.

5. The apparatus of claim 3 in which the encoder/sensor comprises the sensor circuitry, the longitudinal sequence of photosensing elements including at least one of:
   two or more discrete photosensors; and
   two or more photosensing cells in a photosensing array on an integrated circuit (IC).

6. The apparatus of claim 5 in which the longitudinal sequence includes the two or more photosensing cells; the trigger detector including a first set of cells in the photosensing array and the sensor circuitry including a second set of cells in the photosensing array, the trigger detection region being along the first set of cells and the encoding/sensing region being along the second set of cells.

7. The apparatus of claim 5 in which the longitudinal sequence includes the two or more photosensing cells; the circuitry component including the processing circuitry; the processing circuitry providing readout control signals to the IC and, in response, receiving readout quantity signals from the IC that indicate photosensed quantities from cells of the photosensing array.

8. The apparatus of claim 1 in which the circuitry component includes the processing circuitry and the encoder/sensor includes one or both of a photosensor and an impedance-based sensor; the processing circuitry being programmed to perform one or both of:
   in response to the respective trigger signal of an object in the subset, provide readout control signals to the photosensor to obtain readout photosensed quantities; and
   in response to the respective trigger signal of an object in the subset, obtain readout impedance-based quantities from the impedance-based sensor.

9. The apparatus of claim 1 in which the circuitry component includes the control circuitry, the control circuitry including a processor programmed to provide the control signals in response to the object's trigger signal.

10. The apparatus of claim 9 in which the circuitry component further includes the processing circuitry, the processing circuitry also including the processor, the processor also being programmed to obtain the data from the sensing results in response to the object's respective trigger signal.

11. The apparatus of claim 9 in which the control circuitry provides one of:
   control signals only to the encoder/sensor in response to the object's respective trigger signal;
   the relative motion component operating independently of the object's respective trigger signal; and
   control signals both to the encoder/sensor and to the relative motion component.

12. Apparatus comprising:
   an array of photosensing cells on an integrated circuit (IC); the array including first and second sets of photosensing cells; the first set photosensing light emanating from each of a set of distinguishable objects when the object is in a detection region relative to the first set; the second set photosensing light emanating from objects in an encoding/sensing region relative to the second set;
   a relative motion component that causes relative motion of a subset of the distinguishable objects into the detection region, from the detection region into the encoding/sensing region, and within the encoding/sensing region; and
   a circuitry component that:
      reads out photosensed quantities from the first and second sets of photosensing cells; and
      in response to photosensed quantities from the first set indicating light emanating from one of the subset of objects in the detection region, obtains data from photosensed quantities from the second set, the data indicating at least one time-varying waveform with information resulting from the object's relative motion within the encoding/sensing region.

13. A method of using trigger detectors and encoder/sensors, the method including:
   causing relative motion of a distinguishable object into a trigger detection region, from the trigger detection region into an encoding/sensing region, and within the encoding/sensing region; and
   during the relative motion:
      operating a trigger detector to provide a trigger signal when the object is in the trigger detection region; the trigger detection region being relative to the trigger detector;
      operating an encoder/sensor to obtain sensing results when the object is in the encoding/sensing region; the encoding/sensing region being relative to the encoder/sensor; and
      in response to the trigger signal performing at least one of:
         controlling at least one of the encoder/sensor's operation and the object's relative motion within the encoding/sensing region so that the encoder/sensor obtains respective encoded sensing results indicating at least one time-varying waveform with information resulting from the object's relative motion within the encoding/sensing region; and
         obtaining data from the sensing results, the data indicating at least one time-varying waveform with information resulting from the object's relative motion within the encoding/sensing region.

14. The method of claim 13 in which the act of controlling at least one of the encoder/sensor's operation and the object's relative motion includes at least one of:
   providing time-varying excitation in the encoding/sensing region during the object's relative motion within the encoding/sensing region; providing time-varying displacement of the object during the object's relative motion within the encoding/sensing region;
   providing time-varying filtering of light emanating from the encoding/sensing region during the object's relative motion within the encoding/sensing region; and
   obtaining photosensed quantities from a longitudinal sequence of photosensing elements in the encoder/sensor during the object's relative motion within the encoding/sensing region and combining the photosensed quantities to obtain combined encoded sensing results, the combined encoded sensing results indicating a time-varying waveform resulting from the object's relative motion within the encoding/sensing region.

15. The method of claim 14 in which the trigger detector includes a trigger part of an array that includes photosensing cells, the array being on an integrated circuit (IC), the encoder/sensor including a sequence part of the array with two or more of the photosensing cells that are in the longitudinal sequence; the act of operating the trigger detector comprising:
   causing readout of photosensed quantities from the trigger part; and
   the act of controlling at least one of the encoder/sensor's operation and the object's relative motion comprising:
      in response to readout photosensed quantities from the trigger part indicating detection of the object, causing readout of the sequence part.

16. The method of claim 14 in which the encoder/sensor includes an arrangement of discrete photosensors; the act of controlling at least one of the encoder/sensor's operation and the object's relative motion comprising:
   causing readout of the discrete photosensors in the arrangement.

17. The method of claim 13 in which the act of controlling at least one of the encoder/sensor's operation and the object's relative motion comprises:
   providing displacement of the object's relative motion within the encoding/sensing region.

18. The method of claim 17 in which the act of providing displacement includes at least one of:
  controlling flow of fluid carrying the object;
  controlling movement of a channel through which the object is carried by fluid;
  controlling movement of a structure supporting the object; and
  controlling movement of the encoder/sensor.

19. Apparatus comprising:
  a fluidic structure that includes a channel within which objects can have relative motion in a longitudinal direction during operation of the apparatus;
  a trigger detector along the channel upstream from an encoding/sensing region, the trigger detector responding to each of a set of distinguishable objects as the object has relative motion into a trigger detection region relative to the trigger detector, providing a respective trigger signal; and
  an encoder/sensor that responds to the respective trigger signal of an object in the set, obtaining respective sensing results while the object has relative motion within the encoding/sensing region, the respective sensing results indicating at least one time-varying waveform with information resulting from the object's relative motion within the encoding/sensing region; the encoder/sensor including at least one of:
    excitation circuitry that can provide time-varying excitation to objects in the encoding/sensing region;
    each of the objects in the set emanating light in response to the time-varying excitation as the object has relative motion within the encoding/sensing region;
    displacement circuitry that can provide time-varying displacement of objects relative to the channel in the encoding/sensing region;
    each of the objects in the set being displaced relative to the channel as the object has relative motion within the encoding/sensing region;
    filter circuitry that can provide time-varying filtering of light emanating from objects in the encoding/sensing region; and
    sensor circuitry that includes a longitudinal sequence of two or more photosensing elements along the encoding/sensing region and that can read out and combine photosensed quantities from a subsequence of two or more of the photosensing elements to provide combined sensing results as the object has relative motion within the encoding/sensing region and emanates light, the combined sensing results indicating a time-varying waveform with information resulting from the object's relative motion within the encoding/sensing region.

20. The apparatus of claim 19, further comprising:
  control circuitry that receives the trigger signals and, in response, provides control signals that cause the encoder/sensor to obtain the object's respective sensing results; the control circuitry including a processor.

21. The apparatus of claim 19 in which the encoder/sensor includes the filter circuitry; the filter circuitry including liquid crystal display (LCD) circuitry that causes operation of an LCD filter in response to the trigger signals.

22. The apparatus of claim 19, further comprising:
  an integrated circuit (IC) that includes a photosensing array; the trigger detector including a first set of cells in the photosensing array and the sensor circuitry including a second set of cells in the photosensing array, downstream from the first set.

23. The apparatus of claim 19, further comprising:
  an integrated circuit (IC) that includes a photosensing array; and
  a processor that provides readout signals to the IC and, in response, receives from the IC signals that indicate photosensed quantities from cells of the photosensing array.

24. The apparatus of claim 19 in which the apparatus is a flow cytometer.

25. The apparatus of claim 19, further comprising:
  a processing component that, in response to the object's respective sensing results, performs operations to obtain data indicating information resulting from the object's relative motion within the encoding/sensing region.

* * * * *